US010352880B2

(12) United States Patent
Yun et al.

(10) Patent No.: US 10,352,880 B2
(45) Date of Patent: Jul. 16, 2019

(54) METHOD AND APPARATUS FOR X-RAY MICROSCOPY

(71) Applicant: Sigray, Inc., Concord, CA (US)

(72) Inventors: Wenbing Yun, Walnut Creek, CA (US); Sylvia Jia Yun Lewis, San Francisco, CA (US); Janos Kirz, Berkeley, CA (US); Srivatsan Seshadri, Martinez, CA (US); Alan Francis Lyon, Berkeley, CA (US); David Vine, Berkeley, CA (US)

(73) Assignee: Sigray, Inc., Concord, CA (US)

( * ) Notice: Subject to any disclaimer, the term of this patent is extended or adjusted under 35 U.S.C. 154(b) by 12 days.

(21) Appl. No.: 15/605,957

(22) Filed: May 26, 2017

(65) Prior Publication Data
US 2017/0261442 A1    Sep. 14, 2017

Related U.S. Application Data

(63) Continuation-in-part of application No. 15/173,711, filed on Jun. 5, 2016, which is a continuation-in-part
(Continued)

(51) Int. Cl.
*G21K 7/00* (2006.01)
*G01N 23/04* (2018.01)
(Continued)

(52) U.S. Cl.
CPC ........... *G01N 23/04* (2013.01); *A61B 6/4007* (2013.01); *A61B 6/4291* (2013.01); *A61B 6/484* (2013.01);
(Continued)

(58) Field of Classification Search
CPC .............................. G21K 7/00; G21K 2207/00
See application file for complete search history.

(56) References Cited

U.S. PATENT DOCUMENTS

| 1,203,495 | A | 10/1916 | Coolidge |
| 1,211,092 | A | 1/1917 | Coolidge |

(Continued)

FOREIGN PATENT DOCUMENTS

| CN | 102124537 A | 7/2011 |
| EP | 0432568 | 6/1991 |

(Continued)

OTHER PUBLICATIONS

Hennekam et al., "Trace metal analysis of sediment cores using a novel X-ray fluorescence core scanning method," Quaternary Int'l, https://doi.org/10.1016/j.quaint.2018.10.018 (2018).
(Continued)

*Primary Examiner* — Dani Fox
(74) *Attorney, Agent, or Firm* — Knobbe, Martens, Olson & Bear, LLP

(57) ABSTRACT

This disclosure presents systems for x-ray microscopy using an array of micro-beams having a micro- or nano-scale beam intensity profile to provide selective illumination of micro- or nano-scale regions of an object. An array detector is positioned such that each pixel of the detector only detects x-rays corresponding to a single micro- or nano-beam. This allows the signal arising from each x-ray detector pixel to be identified with the specific, limited micro- or nano-scale region illuminated, allowing sampled transmission image of the object at a micro- or nano-scale to be generated while using a detector with pixels having a larger size and scale. Detectors with higher quantum efficiency may therefore be used, since the lateral resolution is provided solely by the dimensions of the micro- or nano-beams. The micro- or nano-scale beams may be generated using an arrayed x-ray source or a set of Talbot interference fringes.

32 Claims, 20 Drawing Sheets

Related U.S. Application Data of application No. 14/712,917, filed on May 15, 2015, now Pat. No. 9,874,531, which is a continuation-in-part of application No. 14/700,137, filed on Apr. 29, 2015, now Pat. No. 9,719,947.

(60) Provisional application No. 62/171,377, filed on Jun. 5, 2015, provisional application No. 62/343,594, filed on May 31, 2016, provisional application No. 62/485,916, filed on Apr. 15, 2017, provisional application No. 62/429,760, filed on Dec. 3, 2016, provisional application No. 62/429,587, filed on Dec. 2, 2016, provisional application No. 62/401,164, filed on Sep. 28, 2016.

(51) Int. Cl.
*G01N 23/20* (2018.01)
*A61B 6/00* (2006.01)
*G21K 1/02* (2006.01)
*H01J 35/08* (2006.01)

(52) U.S. Cl.
CPC ....... *A61B 6/508* (2013.01); *G01N 23/20075* (2013.01); *G21K 1/02* (2013.01); *G21K 7/00* (2013.01); *H01J 35/08* (2013.01); *G01N 2223/3306* (2013.01); *G21K 2207/005* (2013.01); *H01J 2235/086* (2013.01); *H01J 2235/1291* (2013.01)

(56) References Cited

U.S. PATENT DOCUMENTS

| | | |
|---|---|---|
| 1,215,116 A | 2/1917 | Coolidge |
| 1,328,495 A | 1/1920 | Coolidge |
| 1,355,126 A | 10/1920 | Coolidge |
| 1,790,073 A | 1/1931 | Pohl |
| 1,917,099 A | 7/1933 | Coolidge |
| 1,946,312 A | 2/1934 | Coolidge |
| 2,926,270 A | 2/1960 | Zunick |
| 3,795,832 A | 3/1974 | Holland |
| 4,227,112 A | 10/1980 | Waugh et al. |
| 4,266,138 A | 5/1981 | Nelson et al. |
| 4,426,718 A | 1/1984 | Hayashi |
| 4,523,327 A | 6/1985 | Eversole |
| 4,573,186 A | 2/1986 | Reinhold |
| 4,807,268 A | 2/1989 | Wittrey |
| 4,940,319 A | 7/1990 | Ueda et al. |
| 4,951,304 A | 8/1990 | Piestrup et al. |
| 4,972,449 A | 11/1990 | Upadhya et al. |
| 5,001,737 A | 3/1991 | Lewis et al. |
| 5,008,918 A | 4/1991 | Lee et al. |
| 5,132,997 A | 7/1992 | Kojima |
| 5,148,462 A | 9/1992 | Spitsyn et al. |
| 5,173,928 A | 12/1992 | Momose et al. |
| 5,249,216 A | 9/1993 | Ohsugi et al. |
| 5,276,724 A | 1/1994 | Kumasaka et al. |
| 5,602,899 A | 2/1997 | Larson |
| 5,604,782 A | 2/1997 | Cash, Jr. |
| 5,629,969 A | 5/1997 | Koshishiba |
| 5,657,365 A | 8/1997 | Yamamoto et al. |
| 5,682,415 A | 10/1997 | O'Hara |
| 5,715,291 A | 2/1998 | Momose |
| 5,729,583 A | 3/1998 | Tang et al. |
| 5,768,339 A | 6/1998 | O'Hara |
| 5,772,903 A | 6/1998 | Hirsch |
| 5,778,039 A | 7/1998 | Hossain |
| 5,812,629 A | 9/1998 | Clauser |
| 5,825,848 A | 10/1998 | Virshup et al. |
| 5,832,052 A | 11/1998 | Hirose et al. |
| 5,857,008 A | 1/1999 | Reinhold |
| 5,878,110 A | 3/1999 | Yamamoto et al. |
| 5,881,126 A | 3/1999 | Momose |
| 5,912,940 A | 6/1999 | O'Hara |
| 5,930,325 A | 7/1999 | Momose |
| 6,108,397 A | 8/2000 | Cash, Jr. |
| 6,108,398 A | 8/2000 | Mazor et al. |
| 6,125,167 A | 9/2000 | Morgan |
| 6,278,764 B1 | 8/2001 | Barbee, Jr. et al. |
| 6,359,964 B1 | 3/2002 | Kogan |
| 6,377,660 B1 | 4/2002 | Ukita et al. |
| 6,381,303 B1 | 4/2002 | Vu et al. |
| 6,389,100 B1 | 5/2002 | Verman et al. |
| 6,430,254 B2 | 8/2002 | Wilkins |
| 6,442,231 B1 | 8/2002 | O'Hara |
| 6,456,688 B1 | 9/2002 | Taguchi et al. |
| 6,463,123 B1 | 10/2002 | Korenev |
| 6,487,272 B1 | 11/2002 | Kutsuzawa |
| 6,504,902 B2 | 1/2003 | Iwasaki et al. |
| 6,507,388 B2 | 1/2003 | Burghoorn |
| 6,553,096 B1 | 4/2003 | Zhou et al. |
| 6,560,313 B1 | 5/2003 | Harding et al. |
| 6,560,315 B1 | 5/2003 | Price et al. |
| 6,707,883 B1 | 3/2004 | Tiearney et al. |
| 6,711,234 B1 | 3/2004 | Loxley et al. |
| 6,811,612 B2 | 11/2004 | Gruen et al. |
| 6,815,363 B2 | 11/2004 | Yun et al. |
| 6,829,327 B1 | 12/2004 | Chen |
| 6,847,699 B2 | 1/2005 | Rigali et al. |
| 6,850,598 B1 | 2/2005 | Fryda et al. |
| 6,870,172 B1 | 3/2005 | Mankos et al. |
| 6,885,503 B2 | 4/2005 | Yun et al. |
| 6,914,723 B2 | 7/2005 | Yun et al. |
| 6,917,472 B1 | 7/2005 | Yun et al. |
| 6,947,522 B2 | 9/2005 | Wilson et al. |
| 6,975,703 B2 | 12/2005 | Wilson et al. |
| 7,003,077 B2 | 2/2006 | Jen et al. |
| 7,006,596 B1 | 2/2006 | Janik |
| 7,015,467 B2 | 3/2006 | Maldonado et al. |
| 7,023,955 B2 | 4/2006 | Chen et al. |
| 7,057,187 B1 | 6/2006 | Yun et al. |
| 7,079,625 B2 | 7/2006 | Lenz |
| 7,095,822 B1 | 8/2006 | Yun |
| 7,110,503 B1 | 9/2006 | Kumakhov |
| 7,119,953 B2 | 10/2006 | Yun et al. |
| 7,130,375 B1 | 10/2006 | Yun et al. |
| 7,170,969 B1 | 1/2007 | Yun et al. |
| 7,180,979 B2 | 2/2007 | Momose |
| 7,180,981 B2 | 2/2007 | Wang |
| 7,183,547 B2 | 2/2007 | Yun et al. |
| 7,215,736 B1 | 5/2007 | Wang et al. |
| 7,215,741 B2 | 5/2007 | Ukita et al. |
| 7,218,700 B2 | 5/2007 | Huber et al. |
| 7,218,703 B2 | 5/2007 | Yada et al. |
| 7,221,731 B2 | 5/2007 | Yada et al. |
| 7,245,696 B2 | 7/2007 | Yun et al. |
| 7,268,945 B2 | 9/2007 | Yun et al. |
| 7,286,640 B2 | 10/2007 | Yun et al. |
| 7,297,959 B2 | 11/2007 | Yun et al. |
| 7,298,826 B2 | 11/2007 | Inazuru |
| 7,330,533 B2 | 2/2008 | Sampayon |
| 7,346,148 B2 | 3/2008 | Ukita |
| 7,346,204 B2 | 3/2008 | Ito |
| 7,359,487 B1 | 4/2008 | Newcome |
| 7,365,909 B2 | 4/2008 | Yun et al. |
| 7,365,918 B1 | 4/2008 | Yun et al. |
| 7,382,864 B2 | 6/2008 | Hebert et al. |
| 7,388,942 B2 | 6/2008 | Wang et al. |
| 7,394,890 B1 | 7/2008 | Wang et al. |
| 7,400,704 B1 | 7/2008 | Yun et al. |
| 7,406,151 B1 | 7/2008 | Yun |
| 7,412,024 B1 | 8/2008 | Yun et al. |
| 7,412,030 B1 | 8/2008 | O'Hara |
| 7,412,131 B2 | 8/2008 | Lee et al. |
| 7,414,787 B2 | 8/2008 | Yun et al. |
| 7,433,444 B2 | 10/2008 | Baumann |
| 7,443,953 B1 | 10/2008 | Yun et al. |
| 7,453,981 B2 | 11/2008 | Baumann |
| 7,463,712 B2 | 12/2008 | Zhu et al. |
| 7,486,770 B2 | 2/2009 | Baumann |
| 7,492,871 B2 | 2/2009 | Popescu |
| 7,499,521 B2 | 3/2009 | Wang et al. |
| 7,515,684 B2 | 4/2009 | Gibson et al. |

(56) References Cited

U.S. PATENT DOCUMENTS

| | | |
|---|---|---|
| 7,522,698 B2 | 4/2009 | Popescu |
| 7,522,707 B2 | 4/2009 | Steinlage et al. |
| 7,522,708 B2 | 4/2009 | Heismann |
| 7,529,343 B2 | 5/2009 | Safai et al. |
| 7,532,704 B2 | 5/2009 | Hempel |
| 7,551,719 B2 | 6/2009 | Yokhin et al. |
| 7,551,722 B2 | 6/2009 | Ohshima et al. |
| 7,561,662 B2 | 7/2009 | Wang et al. |
| 7,564,941 B2 | 7/2009 | Baumann |
| 7,583,789 B1 | 9/2009 | Macdonald et al. |
| 7,601,399 B2 | 10/2009 | Barnola et al. |
| 7,639,786 B2 | 12/2009 | Baumann |
| 7,646,843 B2 | 1/2010 | Popescu et al. |
| 7,672,433 B2 | 3/2010 | Zhong et al. |
| 7,680,243 B2 | 3/2010 | Yokhin et al. |
| 7,787,588 B1 | 8/2010 | Yun et al. |
| 7,796,725 B1 | 9/2010 | Yun et al. |
| 7,796,726 B1 | 9/2010 | Gendreau et al. |
| 7,800,072 B2 | 9/2010 | Yun et al. |
| 7,813,475 B1 | 10/2010 | Wu et al. |
| 7,817,777 B2 | 10/2010 | Baumann et al. |
| 7,864,426 B2 | 1/2011 | Yun et al. |
| 7,864,922 B2 | 1/2011 | Kawabe |
| 7,873,146 B2 | 1/2011 | Okunuki et al. |
| 7,876,883 B2 | 1/2011 | O'Hara |
| 7,889,838 B2 | 2/2011 | David et al. |
| 7,889,844 B2 | 2/2011 | Okunuki et al. |
| 7,914,693 B2 | 3/2011 | Jeong et al. |
| 7,920,673 B2 | 4/2011 | Lanza et al. |
| 7,920,676 B2 | 4/2011 | Yun et al. |
| 7,924,973 B2 | 4/2011 | Kottler et al. |
| 7,929,667 B1 | 4/2011 | Zhuang et al. |
| 7,945,018 B2 | 5/2011 | Heismann |
| 7,949,092 B2 | 5/2011 | Brons |
| 7,949,095 B2 | 5/2011 | Ning |
| 7,974,379 B1 | 7/2011 | Case et al. |
| 7,983,381 B2 | 7/2011 | David et al. |
| 7,991,120 B2 | 8/2011 | Okunuki et al. |
| 8,005,185 B2 | 8/2011 | Popescu |
| 8,009,796 B2 | 8/2011 | Popescu |
| 8,041,004 B2 | 10/2011 | David |
| 8,036,341 B2 | 11/2011 | Lee |
| 8,058,621 B2 | 11/2011 | Kommareddy et al. |
| 8,068,579 B1 | 11/2011 | Yun et al. |
| 8,073,099 B2 | 12/2011 | Niu et al. |
| 8,094,784 B2 | 1/2012 | Morton |
| 8,139,716 B2 | 3/2012 | Okunuki et al. |
| 8,184,771 B2 | 5/2012 | Murakoshi |
| 8,208,602 B2 | 6/2012 | Lee et al. |
| 8,208,603 B2 | 6/2012 | Sato |
| 8,243,879 B2 | 8/2012 | Itoh et al. |
| 8,243,884 B2 | 8/2012 | Rödhammer et al. |
| 8,280,000 B2 | 10/2012 | Takahashi |
| 8,306,183 B2 | 11/2012 | Koehler |
| 8,306,184 B2 | 11/2012 | Chang et al. |
| 8,351,569 B2 | 1/2013 | Baker |
| 8,351,570 B2 | 1/2013 | Nakamura |
| 8,353,628 B1 | 1/2013 | Yun et al. |
| 8,360,640 B2 | 1/2013 | Reinhold |
| 8,374,309 B2 | 2/2013 | Donath |
| 8,406,378 B2 | 3/2013 | Wang et al. |
| 8,416,920 B2 | 4/2013 | Okumura et al. |
| 8,422,633 B2 | 4/2013 | Lantz et al. |
| 8,451,975 B2 | 5/2013 | Tada |
| 8,422,637 B2 | 6/2013 | Okunuki et al. |
| 8,509,386 B2 | 8/2013 | Lee et al. |
| 8,520,803 B2 | 8/2013 | Behling |
| 8,526,575 B1 | 9/2013 | Yun et al. |
| 8,532,257 B2 | 9/2013 | Mukaide et al. |
| 8,553,843 B2 | 10/2013 | Drory |
| 8,559,597 B2 | 10/2013 | Chen et al. |
| 8,565,371 B2 | 10/2013 | Bredno |
| 8,576,983 B2 | 11/2013 | Baeumer |
| 8,591,108 B2 | 11/2013 | Tada |
| 8,602,648 B1 | 12/2013 | Jacobsen et al. |
| 8,632,247 B2 | 1/2014 | Ishii |
| 8,666,024 B2 | 3/2014 | Okunuki et al. |
| 8,666,025 B2 | 3/2014 | Klausz |
| 8,699,667 B2 | 4/2014 | Steinlage et al. |
| 8,735,844 B1 | 5/2014 | Khaykovich et al. |
| 8,737,565 B1 | 5/2014 | Lyon et al. |
| 8,744,048 B2 | 6/2014 | Lee et al. |
| 8,755,487 B2 | 6/2014 | Kaneko |
| 8,767,915 B2 | 7/2014 | Stutman |
| 8,767,916 B2 | 7/2014 | Hashimoto |
| 8,781,069 B2 | 7/2014 | Murakoshi |
| 8,824,629 B2 | 9/2014 | Ishii |
| 8,831,174 B2 | 9/2014 | Kohara |
| 8,831,175 B2 | 9/2014 | Silver et al. |
| 8,831,179 B2 | 9/2014 | Adler et al. |
| 8,855,265 B2 | 10/2014 | Engel |
| 8,861,682 B2 | 10/2014 | Okunuki et al. |
| 8,903,042 B2 | 12/2014 | Ishii |
| 8,995,622 B2 | 3/2015 | Adler et al. |
| 9,001,967 B2 | 4/2015 | Baturin |
| 9,008,278 B2 | 4/2015 | Lee et al. |
| 9,016,943 B2 | 4/2015 | Jacobsen et al. |
| 9,020,101 B2 | 4/2015 | Omote et al. |
| 9,129,715 B2 | 9/2015 | Adler et al. |
| 9,329,141 B2 | 5/2016 | Stutman |
| 9,357,975 B2 | 6/2016 | Baturin |
| 9,390,881 B2 | 7/2016 | Yun et al. |
| 9,439,613 B2 | 9/2016 | Stutman |
| 9,448,190 B2 | 9/2016 | Yun et al. |
| 9,449,781 B2 | 9/2016 | Yun et al. |
| 9,543,109 B2 | 1/2017 | Yun et al. |
| 9,570,265 B1 | 2/2017 | Yun et al. |
| 9,594,036 B2 | 3/2017 | Yun et al. |
| 9,632,040 B2 | 4/2017 | Stutman |
| 9,719,947 B2 | 8/2017 | Yun et al. |
| 9,823,203 B2 | 11/2017 | Yun et al. |
| 9,874,531 B2 | 1/2018 | Yun et al. |
| 9,939,392 B2 | 4/2018 | Wen |
| 2001/0006413 A1 | 7/2001 | Burghoorn |
| 2002/0085676 A1 | 7/2002 | Snyder |
| 2003/0142790 A1 | 1/2003 | Zhou et al. |
| 2003/0223536 A1 | 12/2003 | Yun et al. |
| 2004/0120463 A1 | 6/2004 | Wilson et al. |
| 2004/0140432 A1 | 7/2004 | Maldonado et al. |
| 2005/0074094 A1 | 4/2005 | Jen et al. |
| 2005/0123097 A1 | 6/2005 | Wang |
| 2005/0163284 A1 | 7/2005 | Inazuru |
| 2005/0282300 A1 | 12/2005 | Yun et al. |
| 2006/0045234 A1* | 3/2006 | Pelc ............... A61B 6/032 378/9 |
| 2006/0062350 A1 | 3/2006 | Yokhin |
| 2007/0030959 A1 | 2/2007 | Ritter |
| 2007/0071174 A1 | 3/2007 | Hebert et al. |
| 2007/0108387 A1 | 5/2007 | Yun et al. |
| 2007/0110217 A1 | 5/2007 | Ukita |
| 2007/0183563 A1 | 8/2007 | Baumann |
| 2007/0183579 A1 | 8/2007 | Baumann et al. |
| 2007/0189449 A1 | 8/2007 | Baumann |
| 2007/0248215 A1 | 10/2007 | Ohshima et al. |
| 2008/0084966 A1 | 4/2008 | Aoki et al. |
| 2008/0089484 A1 | 4/2008 | Reinhold |
| 2008/0094694 A1 | 4/2008 | Yun et al. |
| 2008/0159707 A1 | 7/2008 | Lee et al. |
| 2008/0165355 A1 | 7/2008 | Yasui et al. |
| 2008/0170662 A1 | 7/2008 | Reinhold |
| 2008/0170668 A1 | 7/2008 | Kruit et al. |
| 2008/0181363 A1 | 7/2008 | Fenter et al. |
| 2008/0240344 A1 | 10/2008 | Reinhold |
| 2008/0273662 A1 | 11/2008 | Yun |
| 2009/0052619 A1* | 2/2009 | Endoh ............... G01N 23/04 378/43 |
| 2009/0092227 A1 | 4/2009 | David |
| 2009/0154640 A1 | 6/2009 | Baumann et al. |
| 2009/0316860 A1 | 12/2009 | Okunuki et al. |
| 2010/0012845 A1 | 1/2010 | Baeumer et al. |
| 2010/0027739 A1 | 2/2010 | Lantz et al. |
| 2010/0040202 A1 | 2/2010 | Lee |
| 2010/0046702 A1 | 2/2010 | Chen et al. |
| 2010/0061508 A1 | 3/2010 | Takahashi |

(56) References Cited

U.S. PATENT DOCUMENTS

| | | |
|---|---|---|
| 2010/0091947 A1 | 4/2010 | Niu |
| 2010/0141151 A1 | 6/2010 | Reinhold |
| 2010/0246765 A1 | 9/2010 | Murakoshi |
| 2010/0260315 A1 | 10/2010 | Sato et al. |
| 2010/0272239 A1 | 10/2010 | Lantz et al. |
| 2010/0284513 A1 | 11/2010 | Kawabe |
| 2011/0026680 A1 | 2/2011 | Sato |
| 2011/0038455 A1 | 2/2011 | Silver et al. |
| 2011/0058655 A1 | 3/2011 | Okumura et al. |
| 2011/0064191 A1 | 3/2011 | Toth et al. |
| 2011/0085644 A1 | 4/2011 | Verman |
| 2011/0135066 A1 | 6/2011 | Behling |
| 2011/0142204 A1 | 6/2011 | Zou et al. |
| 2011/0235781 A1 | 9/2011 | Aoki et al. |
| 2011/0243302 A1 | 10/2011 | Murakoshi |
| 2011/0268252 A1 | 11/2011 | Ozawa et al. |
| 2012/0041679 A1 | 2/2012 | Stampanoni |
| 2012/0057669 A1 | 3/2012 | Vogtmeier et al. |
| 2012/0163547 A1 | 6/2012 | Lee et al. |
| 2012/0163554 A1 | 6/2012 | Tada |
| 2012/0224670 A1 | 9/2012 | Kiyohara et al. |
| 2012/0228475 A1 | 9/2012 | Pang et al. |
| 2012/0269323 A1 | 10/2012 | Adler et al. |
| 2012/0269324 A1 | 10/2012 | Adler |
| 2012/0269325 A1 | 10/2012 | Adler et al. |
| 2012/0269326 A1 | 10/2012 | Adler et al. |
| 2012/0294420 A1 | 11/2012 | Nagai |
| 2013/0011040 A1 | 1/2013 | Kido et al. |
| 2013/0032727 A1 | 2/2013 | Kondoe |
| 2013/0039460 A1 | 2/2013 | Levy |
| 2013/0108012 A1 | 5/2013 | Sato |
| 2013/0108022 A1 | 5/2013 | Kugland et al. |
| 2013/0195246 A1 | 8/2013 | Tamura et al. |
| 2013/0223594 A1 | 8/2013 | Sprong et al. |
| 2013/0259207 A1 | 10/2013 | Omote et al. |
| 2013/0279651 A1 | 10/2013 | Yokoyama |
| 2013/0308112 A1 | 11/2013 | Clube et al. |
| 2013/0308754 A1 | 11/2013 | Yamazaki et al. |
| 2014/0023973 A1 | 1/2014 | Marconi et al. |
| 2014/0037052 A1 | 2/2014 | Adler |
| 2014/0064445 A1 | 3/2014 | Adler |
| 2014/0072104 A1 | 3/2014 | Jacobsen et al. |
| 2014/0079188 A1 | 3/2014 | Hesselink et al. |
| 2014/0105363 A1 | 4/2014 | Chen et al. |
| 2014/0146945 A1 | 5/2014 | Fredenberg et al. |
| 2014/0153692 A1 | 6/2014 | Larkin et al. |
| 2014/0177800 A1 | 6/2014 | Sato et al. |
| 2014/0185778 A1 | 7/2014 | Lee et al. |
| 2014/0205057 A1 | 7/2014 | Koehler et al. |
| 2014/0211919 A1 | 7/2014 | Ogura et al. |
| 2014/0226785 A1 | 8/2014 | Stutman et al. |
| 2014/0241493 A1 | 8/2014 | Yokoyama |
| 2014/0270060 A1 | 9/2014 | Date et al. |
| 2014/0369469 A1 | 12/2014 | Ogura et al. |
| 2015/0030126 A1 | 1/2015 | Radicke |
| 2015/0030127 A1 | 1/2015 | Aoki et al. |
| 2015/0043713 A1 | 2/2015 | Chen |
| 2015/0049860 A1 | 2/2015 | Das |
| 2015/0055743 A1 | 2/2015 | Vedantham et al. |
| 2015/0055745 A1 | 2/2015 | Holzner et al. |
| 2015/0092924 A1 | 4/2015 | Yun et al. |
| 2015/0110252 A1 | 4/2015 | Yun et al. |
| 2015/0117599 A1 | 4/2015 | Yun et al. |
| 2015/0194287 A1 | 7/2015 | Yun et al. |
| 2015/0243397 A1 | 8/2015 | Yun et al. |
| 2015/0247811 A1 | 9/2015 | Yun et al. |
| 2015/0260663 A1 | 9/2015 | Yun et al. |
| 2015/0357069 A1 | 12/2015 | Yun et al. |
| 2016/0064175 A1 | 3/2016 | Yun et al. |
| 2016/0066870 A1 | 3/2016 | Yun et al. |
| 2016/0106387 A1 | 4/2016 | Kahn |
| 2016/0178540 A1 | 6/2016 | Yun et al. |
| 2016/0268094 A1 | 9/2016 | Yun et al. |
| 2016/0320320 A1 | 11/2016 | Yun et al. |
| 2016/0351370 A1 | 12/2016 | Yun et al. |
| 2017/0047191 A1 | 2/2017 | Yun et al. |
| 2017/0052128 A1 | 2/2017 | Yun et al. |
| 2017/0162288 A1 | 6/2017 | Yun et al. |
| 2017/0162359 A1 | 6/2017 | Tang et al. |
| 2017/0227476 A1 | 8/2017 | Zhang et al. |
| 2017/0234811 A1 | 8/2017 | Zhang et al. |
| 2017/0261442 A1 | 9/2017 | Yun et al. |
| 2017/0336334 A1 | 11/2017 | Yun et al. |
| 2018/0144901 A1 | 5/2018 | Yun et al. |
| 2018/0261352 A1 | 9/2018 | Matsuyama et al. |
| 2018/0306734 A1 | 10/2018 | Morimoto et al. |

FOREIGN PATENT DOCUMENTS

| | | |
|---|---|---|
| EP | 0751533 | 1/1997 |
| EP | 1028451 | 8/2000 |
| FR | 2548447 | 1/1985 |
| JP | H06-188092 | 7/1994 |
| JP | H07-056000 | 3/1995 |
| JP | H08-184572 | 7/1996 |
| JP | 2000-306533 | 11/2000 |
| JP | 2007-218683 | 8/2007 |
| JP | 2007-265981 | 10/2007 |
| JP | 2007-311185 | 11/2007 |
| JP | 2008-200359 | 4/2008 |
| JP | 2008-197495 | 8/2008 |
| JP | 2009-195349 | 3/2009 |
| JP | 2009-212058 | 9/2009 |
| JP | 2010-236986 | 10/2010 |
| JP | 2011-029072 | 2/2011 |
| JP | 2011-218147 | 11/2011 |
| JP | 2012-187341 | 10/2012 |
| JP | 2013-508683 | 3/2013 |
| JP | 2013-157269 | 8/2013 |
| JP | 2013-160637 | 8/2013 |
| JP | 2013-239317 | 11/2013 |
| JP | 2015-002074 | 1/2015 |
| JP | 2015-047306 | 3/2015 |
| JP | 2015-077289 | 4/2015 |
| WO | WO 1995/006952 | 3/1995 |
| WO | WO 1998/011592 | 3/1998 |
| WO | WO 2002/039792 | 5/2002 |
| WO | WO 2003/081631 | 10/2003 |
| WO | WO 2005/109969 | 11/2005 |
| WO | WO 2006/096052 | 9/2006 |
| WO | WO 2007/125833 | 11/2007 |
| WO | WO 2009/098027 | 8/2009 |
| WO | WO 2009/1104560 | 8/2009 |
| WO | WO 2011/032572 | 3/2011 |
| WO | WO 2012/032950 | 3/2012 |
| WO | WO 2013/004574 | 1/2013 |
| WO | WO 2013/111050 | 8/2013 |
| WO | WO 2013/118593 | 8/2013 |
| WO | WO 2013/160153 | 10/2013 |
| WO | WO 2013/168468 | 11/2013 |
| WO | WO 2014/054497 | 4/2014 |
| WO | WO 2015/016019 | 2/2015 |
| WO | WO 2015/034791 | 3/2015 |
| WO | WO 2015/066333 | 5/2015 |
| WO | WO 2015/084466 | 6/2015 |
| WO | WO 2015/168473 | 11/2015 |
| WO | WO 2015/176023 | 11/2015 |
| WO | WO 2015/187219 | 12/2015 |
| WO | WO 2016/187623 | 11/2016 |
| WO | WO 2017/031740 | 3/2017 |
| WO | WO 2017/204850 | 11/2017 |
| WO | WO 2017/213996 | 12/2017 |
| WO | WO 2018/175570 | 9/2018 |

OTHER PUBLICATIONS

Malzer et al., "A laboratory spectrometer for high throughput X-ray emission spectroscopy in catalysis research," Rev. Sci. Inst. 89, 113111 (2018).

Tkachuk et al., "High-resolution x-ray tomography using laboratory sources", in Developments in X-Ray Tomography V, Proc. SPIE 6318 (2006): 631810.

(56) References Cited

OTHER PUBLICATIONS

Tkachuk et al., "Multi-length scale x-ray tomography using laboratory and synchrotron sources", Microsc. Microanal. vol. 13 (Suppl. 2) (2007), pp. 1570-1571.
Viermetz et al., "High resolution laboratory grating-based X-ray phase-contrast CT," Scientific Reports 8:15884 (2018).
"Diamond," Section 10.4.2 of Zorman et al., "Material Aspects of Micro-Nanoelectromechanical Systems," Chapter 10 of Springer Handbook of Nanotechnology, 2nd ed., Barat Bushan, ed. (Springer Science + Business Media, Inc., New York, 2007), pp. 312-314.
"Element Six CVD Diamond Handbook" (Element Six, Luxembourg, 2015).
"High performance benchtop EDXRF spectrometer with Windows® software," published by: Rigaku Corp., Tokyo, Japan; 2017.
"Monochromatic Doubly Curved Crystal Optics," published by: X-Ray Optical Systems, Inc. (XOS), East Greenbush, NY; 2017.
"Optics and Detectors," Section 4 of XS-Ray Data Booklet, 3rd Ed., A.C. Thompson ed. (Lawrence Berkeley Nat'l Lab, Berkeley, CA, 2009).
"Properties of Solids," Ch. 12 of CRC Handbook of Chemistry and Physics, 90th ed., Devid R. Lide & W.M. "Mickey" Haynes, eds. (CRC Press, Boca Raton, FL, 2009), pp. 12-41-12-46; 12-203-12-212.
"Science and Technology of Future Light Sources", Arthur L. Robinson (LBNL) and Brad Plummer (SLAG), eds. Report Nos. ANL-08/39 / BNL-81895-2008 / LBNL-1090E-2009 / SLAC-R-917 (Lawrence Berkeley Nal'l Lab, Berkeley, CA, Dec. 2008).
"Series 5000 Packaged X-ray Tubes," Product Technical Data Sheet DS006 Rev. G, X-Ray Technologies Inc. (Oxford Insstruments), Scotts Valley, CA (no date).
"Toward Control of Matter: Energy Science Needs for a New Class of X-Ray Light Sources" (Lawrence Berkeley Nal'l Lab, Berkeley, CA, Sep. 2008).
"X-ray Optics for BES Light Source Facilities," Report of the Basic Energy Sciences Workshop on X-ray Optics for BES Light Source Facilities, D. Mills & H. Padmore, Co-Chairs, (U.S. Dept. of Energy, Office of Science, Potomac, MD, Mar. 2013).
Abullian et al., "Quantitative determination of the lateral density and intermolecular correlation between proteins anchored on the membrane surfaces using grazing incidence small-angle X-ray scattering and grazing incidence X-ray fluorescence," Nov. 28, 2012, The Journal of Chemical Physics, vol. 137, pp. 204907-1 to 204907-8.
Adachi et al., "Development of the 17-inch Direct-Conversion Dynamic Flat-panel X-ray Detector (FPD)," Digital R/F (Shimadzu Corp., 2 pages (no date, published-2004 with product release).
Aharonovich et al., "Diamond Nanophotonics," Adv. Op. Mat'ls vol. 2, Issue 10 (2014).
Als-Nielsen et al., "Phase contrast imaging" Sect. 9.3 of Ch. 9 of "Elements of Modern X-ray Physics, Second Edition" , (John Wiley & Sons Ltd, Chichester, West Sussex, UK, 2011), pp. 318-329.
Als-Nielsen et al., "Photoelectric Absorption," Ch. 7 of "Elements of Modern X-ray Physics, Second Edition," (John Wiley & Sons Ltd, Chichester, West Sussex, UK, 2011).
Als-Nielsen et al., "Refraction and reflection from interfaces," Ch. 3 of "Elements of Modern X-ray Physics, Second Edition," (John Wiley & Sons Ltd., Chichester, West Sussex, UK, 2011), pp. 69-112.
Als-Nielsen et al., "X-rays and their interaction with matter", and "Sources", Ch. 1 & 2 of "Elements of Modern X-ray Physics, Second Edition" (John Wiley & Sons Ltd, Chichester, West Sussex, UK, 2011).
Altapova et al., "Phase contrast laminography based on Talbot interferometry," Opt. Express, vol. 20, No. 6, (2012) pp. 6496-6508.
Ando et al., "Smooth and high-rate reactive ion etching of diamond," Diamond and Related Materials, vol. 11, (2002) pp. 824-827.
Arfelli et al., "Mammography with Synchrotron Radiation: Phase-Detection Techniques," Radiology vol. 215, (2000), pp. 286-293.
Arndt et al., Focusing Mirrors for Use with Microfocus X-ray Tubes, 1998, Journal of Applied Crystallography, vol. 31, pp. 733-741.
Balaic et al., "X-ray optics of tapered capillaries," Appl. Opt. vol. 34 (Nov. 1995) pp. 7263-7272.
Baltes et al., "Coherent and incoherent grating reconstruction," J. Opt. Soc. Am. A vol. 3(8), (1986), pp. 1268-1275.
Barbee Jr., "Multilayers for x-ray optics," Opt. Eng. vol. 25 (Aug. 1986) pp. 898-915.
Baron et al., "A compact optical design for Bragg reflections near backscattering," J. Synchrotron Rad., vol. 8 (2001), pp. 1127-1130.
Bech, "In-vivo dark-field and phase-contrast x-ray imaging," Scientific Reports 3, (2013), Article No. 03209.
Bech, "X-ray imaging with a grating interferometer," University of Copenhagan PhD. Thesis, (May 1, 2009).
Bergamin et al., "Measuring small lattice distortions in Si-crystals by phase-contrast x-ray topography," J. Phys. D: Appl. Phys. vol. 33 (Dec. 31, 2000) pp. 2678-2682.
Bernstorff, "Grazing Incidence Small Angle X-ray Scattering (GISAXS)," Presentation at Advanced School on Synchrotron and Free Electron Laser Sources and their Multidisciplinary Applications, Apr. 2008, Trieste, Italy.
Bilderback et al., "Single Capillaries," Ch. 29 of "Handbook of Optics vol. III, 2nd Ed." (McGraw Hill, New York, 2001).
Birkholz, "Chapter 4: Grazing Incidence Configurations," Thin Film Analysis by X-ray Scattering (Wiley-VCH Verlag GmbH & Co. KGaA, Weinheim, Germany, 2006).
Bjeoumikhov et al., "A modular system for XRF and XRD applications consisting of a microfocus X-ray source and different capillary optics," X-ray Spectrometry, vol. 33 (2004), pp. 312-316.
Bjeoumikhov et al., "Capillary Optics for X-Rays," Ch. 18 of "Modern Developments in X-Ray and Neutron Optics," A. Erko et al., eds. (Springer, Berlin, Germany, 2008), pp. 287-306.
Canberra Model S-5005 WinAxil X-Ray Analysis Software, published by: Canberra Eurisys Benelux N.V./S.A.,Zellik, Belgium; Jun. 2004.
Cerrina, "The Schwarzschild Objective," Ch. 27 of "Handbook of Optics vol. III, 2nd Ed." (McGraw Hill, New York, 2001).
Chen et al., "Advance in detection of low sulfur content by wavelength dispersive XRF," Proceedings of the Annual ISA Analysis Division Symposium (2002).
Chen et al., "Doubly curved crystal (DCC) X-ray optics and applications," Powder Diffraction, vol. 17(2) (2002), pp. 99-103.
Chen et al., "Guiding and focusing neutron beams using capillary optics," Nature vol. 357 (Jun. 4, 1992), pp. 391-393.
Chervenak et al., "Experimental thick-target bremsstrahlung spectra from electrons in the range 10 to 30 keV", Phys. Rev. A vol. 12 (1975), pp. 26-33.
Coan et al., "In vivo x-ray phase contrast analyzer-based imaging for longitudinal osteoarthritis studies in guinea pigs," Phys. Med. Biol. vol. 55(24) (2010), pp. 7649-7662.
Cockcroft et al., "Chapter 2: Experimental Setups," Powder Diffraction: Theory and Practice, R.E. Dinnebier and S.J.L. Billinge, eds (Royal Society of Chemistry Publishing, London, UK, 2008).
Cohen et al., "Tunable laboratory extended x-ray absorption fine structure system," Rev. Sci. Instr. vol. 51, No. 3, Mar. 1980, pp. 273-277.
Cong et al., "Fourier transform-based iterative method for differential phase-contrast computed tomography", Opt. Lett. vol. 37 (2012), pp. 1784-1786.
Cornaby et al., "Advances in X-ray Microfocusing with Monocapillary Optics at CHESS," CHESS News Magazine (2009), pp. 63-66.
Cornaby et al., "Design of Single-Bounce Monocapillary X-ray Optics," Advances in X-ray Analysis: Proceedings of the 55th Annual Conference on Applications of X-ray Analysis, vol. 50, (International Centre for Diffraction Data (ICDD), 2007), pp. 194-200.
Cornaby, "The Handbook of X-ray Single Bounce Monocapillary Optics, Including Optical Design and Synchrotron Applications" (PhD Dissertation, Cornell University, Ithaca, NY, May 2008).
David et al., "Fabrication of diffraction gratings for hard x-ray phase contrast imaging," Microelectron. Eng. vol. 84, (2007), pp. 1172-1177.

(56) References Cited

OTHER PUBLICATIONS

David et al., "Hard X-ray phase imaging and tomography using a grating interferometer," Spectrochimica Acta Part B vol. 62 (2007) pp. 626-630.
Davis et al., "Bridging the Micro-to-Macro Gap: A New Application for Micro X-Ray Fluorescence," Microsc Microanal., vol. 17(3) (Jun. 2011), pp. 410-417.
Diaz et al., "Monte Carlo Simulation of Scatter Field for Calculation of Contrast of Discs in Synthetic CDMAM Images," In: Digital Mammography, Proceedings 10th International Workshop IWDM 2010 (Springer Verlag, Berlin Heidelberg), (2010), pp. 628-635 (9 pages). Jun. 18, 2010.
Ding et al., "Reactive Ion Etching of CVD Diamond Films for MEMS Applications," Micromachining and Microfabrication, Proc. SPIE vol. 4230 (2000), pp. 224-230.
Dobrovinskaya et al., "Thermal Properties," Sect. 2.1.5 of "Sapphire: Material, Manufacturing,, Applications" (Springer Science + Business Media, New York, 2009).
Dong et al., "Improving Molecular Sensitivity in X-Ray Fluorescence Molecular Imaging (XFMI) of Iodine Distribution in Mouse-Sized Phantoms via Excitation Spectrum Optimization," IEEE Access, vol. 6, pp. 56966-56976 (2018).
Erko et al., "X-ray Optics," Ch. 3 of "Handbook of Practical X-Ray Fluorescence Analysis," B. Beckhoff et al., eds. (Springer, Berlin, Germany, 2006), pp. 85-198.
Falcone et al., "New directions in X-ray microscopy," Contemporary Physics, vol. 52, No. 4, (Jul.-Aug. 2010), pp. 293-318.
Fernández-Ruiz, "TXRF Spectrometry as a Powerful Tool for the Study of Metallic Traces in Biological Systems," Development in Analytical Chemistry, vol. 1 (2014), pp. 1-14.
Freund, "Mirrors for Synchrotron Beamlines," Ch. 26 of "Handbook of Optics vol. III, 2nd Ed." (McGraw Hill, New York, 2001).
Ge et al., "Investigation of the partially coherent effects in a 2D Talbot interferometer," Anal. Bioanal. Chem. vol. 401, (2011), pp. 865-870. Apr. 29, 2011, pub Jun. 14, 2011.
Gibson et al., "Polycapillary Optics: An Enabling Technology for New Applications," Advances in X-ray Analysis, vol. 45 (2002), pp. 286-297.
Gonzales et al., "Angular Distribution of Bremsstrahlung Produced by 10-Kev and 20 Kev Electrons Incident On A Thick Au Target", in Application of Accelerators in Research and Industry, AIP Conf. Proc. 1221 (2013), pp. 114-117.
Gonzales et al., "Angular distribution of thick-target bremsstrahlung produced by electrons with initial energies ranging from 10 to 20 keV incident on Ag", Phys. Rev. A vol. 84 (2011): 052726.
Guttmann et al., "Ellipsoidal capillary as condenser for the BESSSY full-field x-ray microscope," J. Phys. Conf. Ser. vol. 186 (2009): 012064.
Harasse et al., "Iterative reconstruction in x-ray computed laminography from differential phase measurements", Opt. Express. vol. 19 (2011), pp. 16560-16573.
Harasse et al., "X-ray Phase Laminography with a Grating Interferometer using Iterative Reconstruction", in International Workshop on X-ray and Neutron Phase Imaging with Gratings, AIP Conf. Proc. vol. 1466, (2012), pp. 163-168.
Harasse et al., "X-ray Phase Laminography with Talbot Interferometer", in Developments in X-Ray Tomography VII, Proc. SPIE vol. 7804 (2010), 780411.
Hasse et al., "New developments in laboratory-based x-ray sources and optics," Adv. In Laboratory-based X-Ray Sources, Optics, and Applications VI, ed. A.M. Khounsary, Proc. SPIE vol. 10387, 103870B-1 (2017).
Hemraj-Benny et al., "Near-Edge X-ray Absorption Fine Structure Spectroscopy as a Tool for Investigating Nanomaterials," Small, vol. 2(1), (2006), pp. 26-35.
Henke et al., "X-ray interactions: photoabsorption, scattering, transmission, and reflection at E=50-30000 eV, Z=1-92," Atomic Data and Nuclear Data Tables, vol. 54 (No. 2) (Jul. 1993), pp. 181-342.

Honma et al., Full-automatic XAFS Measurement System of the Engineering Science Research II beamline BL14B2 at Spring-8, 2011, AIP Conference Proceedings 1234, pp. 13-16.
Howard et al., "High-Definition X-ray Fluorescence Elemental Mapping of Paintings," Anal. Chem., 2012, vol. 84(7), pp. 3278-3286.
Howells, "Gratings and Monochromators in the VUV and Soft X-Ray Spectral Region," Ch. 21 of Handbook of Optics vol. III, 2nd Ed. (McGraw Hill, New York, 2001).
Howells, "Mirrors for Synchrotron-Radiation Beamlines," Publication LBL-34750 (Lawrence Berkeley Laboratory, Berkeley, CA, Sep. 1993).
Hrdý et al, "Diffractive-Refractive Optics: X-ray Crystal Monochromators with Profiled Diffracting Surfaces," Ch. 20 of "Modern Developments in X-Ray and Neutron Optics," A. Erko et al., eds. (Springer, Berlin Heidelberg New York, 2008).
Hwang et al, "New etching process for device fabrication using diamond," Diamond & Related Materials, vol. 13 (2004) pp. 2207-2210.
Ide-Ektessabi et al., "The role of trace metallic elements in neurodegenerative disorders: quantitative analysis using XRF and XANES spectroscopy," Anal. Sci., vol. 21(7) (Jul. 2005), pp. 885-892.
Ihsan et al., "A microfocus X-ray tube based on a microstructured X-ray target", Nuclear Instruments and Methods in Physics Research B vol. 267 (2009) pp. 3566-3573.
Ishisaka et al., "A New Method of Analyzing Edge Effect in Phase Contrast Imaging with Incoherent X-rays," Optical Review, vol. 7, No. 6, (2000), pp. 566-572.
Ito et al., "A Stable In-Laboratory EXAFS Measurement System," Jap. J. Appl. Phys., vol. 22, No. 2, Feb. 1, 1983, pp. 357-360.
Itoh et al., "Two-dimensional grating-based X-ray phase-contrast imaging using Fourier transform phase retrieval," Op. Express, vol. 19, No. 4 (2011) pp. 3339-3346.
Janssens et al, "Recent trends in quantitative aspects of microscopic X-ray fluorescence analysis," TrAC Trends in Analytical Chemistry 29.6 (Jun. 2010): 464-478.
Jiang et al., "X-Ray Phase-Contrast Imaging with Three 2D Gratings," Int. J. Biomed. Imaging, (2008), 827152, 8 pages.
Joy, "Astronomical X-ray Optics," Ch. 28 of "Handbook of Optics vol. III, 2nd Ed.," (McGraw Hill, New York, 2001).
Keyrilainen et al., "Phase contrast X-ray imaging of breast," Acta Radiologica, vol. 51 (8), (2010), pp. 866-884. Jan. 18, 2010, pub Jun. 15, 2010.
Kidalov et al., "Thermal Conductivity of Diamond Composites," Materials, vol. 2 (2009) pp. 2467-2495.
Kido et al., "Bone Cartilage Imaging with X-ray Interferometry using a Practical X-ray Tube", in Medical Imaging 2010: Physics of Medical Imaging, Proc. SPIE vol. 7622 (2010), 762240.
Kim, "Talbot images of wavelength-scale amplitude gratings," Opt. Express vol. 20(5), (2012), pp. 4904-4920.
Kirkpatrick et al., "Formation of Optical Images by X-Rays", J. Opt. Soc. Am. vol. 38(9) (1948), pp. 766-774.
Kirz, "Phase zone plates for x rays and the extreme uv," J. Op. Soc. Am. vol. 64 (Mar. 1974), pp. 301-309.
Kirz et al., "The History and Future of X-ray Microscopy", J. Physics: Conden. Series vol. 186 (2009): 012001.
Kiyohara et al., "Development of the Talbot-Lau Interferometry System Available for Clinical Use", in International Workshop on X-ray and Neutron Phase Imaging with Gratings, AIP Cong. Proc. vol. 1466, (2012), pp. 97-102.
Klockenkämper et al., "7.1 Instrumental Developments" and "7.3 Future Prospects by Combinations," from Chapter 7 of Total Reflection X-ray Fluorescence Analysis and Related Methods 2nd Ed. (J. Wiley and Sons, Hoboken, NJ, 2015).
Klockenkämper et al., "Chapter 3: Instrumentation for TXRF and GI-XRF," Total Reflection X-ray Fluorescence Analysis and Related Methods 2nd Ed. (J. Wiley and Sons, Hoboken, NJ, 2015).
Kottler et al., "A two-directional approach for grating based differential phase contrast imaging using hard x-rays," Opt. Express vol. 15(3), (2007), pp. 1175-1181.

(56) References Cited

OTHER PUBLICATIONS

Kottler et al., "Dual energy phase contrast x-ray imaging with Talbot-Lau interferometer," J. Appl. Phys. vol. 108(11), (2010), 114906. Jul. 7, 2010, pub Jul. 12, 2010.
Kumakhov et al., "Multiple reflection from surface X-ray optics," Physics Reports, vol. 191(5), (1990), pp. 289-350.
Kumakhov, "X-ray Capillary Optics. History of Development and Present Status" in Kumakhov Optics and Application, Proc. SPIE 4155 (2000), pp. 2-12.
Kuwabara et al., "Hard-X-ray Phase-Difference Microscopy with a Low-Brilliance Laboratory X-ray Source", Appl. Phys. Express vol. 4 (2011) 062502.
Kuznetsov, "X-Ray Optics Calculator," Institute of Microelectronics Technology and High Purity Materials, Russian Academy of Sciences (IMT RAS), Chernogolovka, Russia (6 pages submitted); 2016.
Lagomarsino et al., "Reflective Optical Arrays," Ch. 19 of "Modern Developments in X-Ray and Neutron Optics," A. Erko et al. eds. (Springer, Berlin, Germany, 2008), pp. 307-317.
Lai, "X-Ray Microfocusing Optics," Slide Presentation from Argonne National Laboratory, 71 slides, Cheiron Summer School 2007.
Langhoff et al., "X-ray Sources," Ch. 2 of "Handbook of Practical X-Ray Fluorescence Analysis," B. Beckhoff et al., eds. (Springer, Berlin Heidelberg New York, 2006), pp. 33-82.
Lechner et al., "Silicon drift detecors for high count rate X-ray spectroscopy at room temperature," Nuclear Instruments and Methods, vol. 458A (2001), pp. 281-287.
Leenaers et al., "Application of Glancing Incidence X-ray Analysis," 1997, X-ray Spectrometry, vol. 26, pp. 115-121.
Lengeler et al., "Refractive X-ray Optics," Ch. 20 of "Handbook of Optics vol. III, 2nd Ed." (McGraw Hill, New York, 2001.
Li et al., "Source-optic-crystal optimisation for compact monochromatic imaging," Proc. SPIE 5537 (2004), pp. 105-114.
Lohmann et al., "An interferometer based on the Talbot effect," Optics Communications vol. 2 (1971), pp. 413-415.
Macdonald et al., "An Introduction to X-ray and Neutron Optics," Ch. 19 of "Handbook of Optics vol. III, 2nd Ed." (McGraw Hill, New York, 2001).
Macdonald et al., "Polycapillary and Multichannel Plate X-Ray Optics," Ch. 30 of "Handbook of Optics vol. III, 2nd Ed.," (McGraw Hill, New York, 2001).
Macdonald et al., "Polycapillary X-ray Optics for Microdiffraction," J. Appl. Cryst., vol. 32 (1999) pp. 160-167.
Macdonald, "Focusing Polycapillary Optics and Their Applications," X-Ray Optics and Instrumentation, vol. 2010, (Oct. 2010): 867049.
Maj et al., "Etching methods for improving surface imperfections of diamonds used for x-ray monochromators," Adv. X-ray Anal., vol. 48 (2005), pp. 176-182.
Malgrange, "X-ray Optics for Synchrotron Radiation," ACTA Physica Polinica A, vol. 82(1) (1992) pp. 13-32.
Masuda et al., "Fabrication of Through-Hole Diamond Membranes by Plasma Etching Using Anodic Porous Alumina Mask," Electrochemical and Solid-State Letters, vol. 4(11) (2001) pp. G101-G103.
Matsushita, "Mirrors and Multilayers," Slide Presentation from Photon Factor, Tsukuba, Japan, 65 slides, (Cheiron School 2009, Sprint-8, Japan, Nov. 2009).
Matsushita, "X-ray monochromators," Slide Presentation from Photon Factory, Tsukuba, Japan, 70 slides, (Cheiron School 2009, Spring-8, Japan, Nov. 2009).
Matsuyama et al., "Wavefront measurement for a hard-X-ray nanobeam using single-grating interferometry", Opt Express vol. 20 (2012), pp. 24977-24986.
Miao et al., "Motionless phase stepping in X-ray phase contrast imaging with a compact source," Proceedings of the National Academy of Sciences, vol. 110(48), (2013), pp. 19268-19272.
Michette, "Zone and Phase Plates, Bragg-Fresnel Optics," Ch. 23 of "Handbook of Optics vol. III, 2nd Ed.," (McGraw Hill, New York, 2001).

Mizutani et al., X-ray microscopy for neural circuit reconstruction in 9th International Conference on X-Ray Microscopy, J. Phys: Conf. Ser. 186 (2009) 012092.
Modregger et al., "Grating-Based X-ray Phase Contrast Imaging," Ch. 3 of Emerging Imaging Technologies in Medicine, M. Anastasio & P. La Riviere, ed., CRC Press, Boca Raton, FL, (2012), pp. 43-56.
Momose et al., "Biomedical Imaging by Talbot-Type X-Ray Phase Tomography" in Developments in X-Ray Tomography V, Proc. SPIE vol. 6318 (2006) 63180T.
Momose et al., "Grating-Based X-ray Phase Imaging Using Multiline X-ray Source", Jpn. J. Appl. Phys. vol. 48 (2009), 076512.
Momose et al., "Phase Tomography by X-ray Talbot Interferometry for Biological Imaging" Jpn. J. Appl. Phys. vol. 45 2006 pp. 5254-5262.
Momose et al., "Phase Tomography Using X-ray Talbot Interferometer", in Synchrotron Radiation Instrumentation: Ninth International Conference, AIP Conf. Proc. vol. 879 (2007), pp. 1365-1368.
Momose et al., "Phase-Contrast X-Ray Imaging Using an X-Ray Interferometer for Biological Imaging", Analytical Sciences vol. 17 Supplement (2001), pp. i527-i530.
Momose et al., "Sensitivity of X-ray Phase Imaging Based on Talbot Interferometry", Jpn. J. Appl. Phys. vol. 47 (2008), pp. 8077-8080.
Momose et al., "X-ray Phase Measurements with Talbot Interferometry and Its Applications", in International Conference on Advanced Phase Measurement Methods in Optics and Imaging, AIP Conf. Proc. vol. 1236 (2010), pp. 195-199.
Momose et al., "X-ray Phase Imaging—From Static Observation to Dynamic Observation-", in International Workshop on X-ray and Neutron Phase Imaging with Gratings AIP Conf. Proc. vol. 1466, (2012), pp. 67-77.
Momose et al., "X-ray Phase Imaging Using Lau Effect", Appl. Phys. Express vol. 4 (2011) 066603.
Momose et al., "X-Ray Phase Imaging with Talbot Interferometry", in "Biomedical Mathematics: Promising Directions in Imaging, Therapy Planning, and Inverse Problems", Y. Censor, M. Jiang & G.Wang, eds. (Medical Physics Publishing, Madison, WI, USA, 2010), pp. 281-320.
Momose et al., "X-ray phase tomography with a Talbot interferometer in combination with an X-ray imaging microscope", in 9th International Conference on X-Ray Microscopy, J. Phys: Conf. Ser. 186 (2009) 012044.
Momose et al., "X-ray Talbot Interferometry with Capillary Plates", Jpn. J. Appl. Phys. vol. 45 (2006), pp. 314-316.
Momose et al., "Four-dimensional X-ray phase tomography with Talbot interferometry and white synchrotron radiation: dynamic observation of a living worm", Opt. Express vol. 19 (2011), pp. 8423-8432.
Momose et al., "High-speed X-ray phase imaging and X-ray phase tomography with Talbot interferometer and white synchrotron radiation", Opt. Express vol. 17 (2009), pp. 12540-12545.
Momose et al., "Phase Imaging with an X-ray Talbot Interferometer", Advances in X-ray Analysis vol. 49(3) (2006), pp. 21-30.
Momose et al.,"Demonstration of X-Ray Talbot Interferometry", Jpn. J. Appl. Phys. vol. 42 (2003), pp. L866-L868.
Momose et al.,"Phase Tomography Using an X-ray Talbot Interferometer", in Developments in X-Ray Tomography IV, Proc. SPIE vol. 5535 (2004), pp. 352-360.
Momose, "Recent Advances in X-ray Phase Imaging", Jpn. J. Appl. Phys. vol. 44 (2005), pp. 6355-6367.
Montgomery, "Self Imaging Objects of Infinite Aperture," J. Opt. Soc. Am. vol. 57(6), (1967), pp. 772-778.
Morimoto et al., "Development of multiline embedded X-ray targets for X-ray phase contrast imaging," XTOP 2012 Book of Abstracts, (Ioffe Physical-Technical Institute of the Russian Academy of Sciences, St. Petersburg, Russia, 2012), pp. 74-75.
Morimoto et al., X-ray phase contrast imaging by compact Talbot-Lau interferometer with a signal transmission grating, 2014, Optics Letters, vol. 39, No. 15, pp. 4297-4300.
Munro et al., Design of a novel phase contrast imaging system for mammography, 2010, Physics in Medicine and Biology, vol. 55, No. 14, pp. 4169-4185.

(56) References Cited

OTHER PUBLICATIONS

Nango et al., "Talbot-defocus multiscan tomography using the synchrotron X-ray microscope to study the lacuno-canalicular network in mouse bone", Biomed. Opt. Express vol. 4 (2013), pp. 917-923.
Neuhausler et al., "Non-destructive high-resolution X-ray imaging of ULSI micro-electronics using keV X-ray microscopy in Zernike phase contrast," Microelectronic Engineering, Elsevier Publishers BV., Amsterdam, NO, vol. 83, No. 4-9 (Apr. 1, 2006) pp. 1043-1046.
Newville, "Fundamentals of XAFS," (Univ. of Chicago, Chicago, IL, Jul. 23, 2004).
Noda et al., "Fabrication of Diffraction Grating with High Aspect Ratio Using X-ray Lithography Technique for X-ray Phase Imaging," Jpn. J. Appl. Phys. vol. 46, (2007), pp. 849-851.
Noda et al., "Fabrication of High Aspect Ratio X-ray Grating Using X-ray Lithography" J. Solid Mech_ Mater. Eng. vol. 3 (2009), pp. 416-423.
Nojeh, "Carbon Nanotube Electron Sources: From Electron Beams to Energy Conversion and Optophononics", ISRN Nanomaterials vol. 2014 (2014): 879827.
Nuhn, "From storage rings to free electron lasers for hard x-rays", J.A37 Phys.: Condens. Matter vol. 16 (2004), pp. S3413-S34121.
Nykanen et al., "X-ray scattering in full-field digital mammography," Med. Phys. vol. 30(7), (2003), pp. 1864-1873.
Oji et al., Automatic XAFS measurement system developed at BL14B2 in SPring-8, Available online Nov. 15, 2011, Journal of Synchrotron Radiation, vol. 19, pp. 54-59.
Olbinado et al., "Demonstration of Stroboscopic X-ray Talbot Interferometry Using Polychromatic Synchrotron and Laboratory X-ray Sources", Appl. Phys. Express vol. 6 (2013), 096601.
Ortega et al., "Bio-metals imaging and speciation in cells using proton and synchrotron radiation X-ray microspectroscopy," J. Royal Society Interface vol. 6 suppl. 5 (Oct. 6, 2009), pp. 6S649-6S658.
Otendal et al., A 9 keV electron-impact liquid-gallium-jet x-ray source, Rev. Sci. Instrum. vol. 79 (2008): 016102.
Oxford Instruments Inc., Series 5000 Model XTF5011 X-ray Tube information, Jun. 1998, 3 pages.
Parrill et al., "GISAXS—Glancing Incidence Small Angle X-ray Scattering," Journal de Physique IV, vol. 3 (Dec. 1993), pp. 411-417.
Paxscan Flat Panel X-ray Imaging, Varian Sales Brochure, (Varian Medical Systems, Palo Alto, CA, Nov. 11, 2004).
Pfeiffer et al., "Hard-X-ray dark-field imaging using a grating interferometer," Nature Materials vol. 7, (2008), pp. 134-137.
Pfeiffer et al., "Hard x-ray phase tomography with low brilliance x-ray sources," Phys. Rev. Lett. vol. 98, (2007), 108105.
Pfeiffer et al., "Phase retrieval and differential phase-contrast imaging with low-brilliance X-ray sources," Nature Physics vol. 2, (2006), pp. 258-261.
Pfeiffer, "Milestones and basic principles of grating-based x-ray and neutron phase-contrast imaging," in International Workshop on X-ray and Neutron Phase Imaging with Gratings AIP Conf. Proc. vol. 1466, (2012), pp. 2-11.
Pianetta et al., "Application of synchrotron radiation to TXRF analysis of metal contamination on silicon wafer surfaces," Thin Solid Films, vol. 373(1-2), 2000, pp. 222-226.
Potts, "Electron Probe Microanalysis", Ch. 10 of "A Handbook of Silicate Rock Analysis" (Springer Science + Business Media, New York, 1987), pp. 326-382 (equation quoted from p. 336).
Prewitt et al., "FIB Repair of 5X Recticles and Effects on IC Quality," Integrated Circuit Metrology, Inspection, and Process Control VII, Proc. SPIE vol. 1926 (1993), pp. 517-526.
Prewitt et al., "Focused ion beam repair: staining of photomasks and reticles," J. Phys. D Appl. Phys. vol. 26 (1993), pp. 1135-1137.
Prewitt et al., "Gallium Staining in FIB Repair of Photomasks," Microelectronic Engineering, vol. 21 (1993), pp. 191-196.
Qin et al., "Trace metal imaging with high spatial resolution: Applications in biomedicine," Metallomics, vol. 3 (Jan. 2011), pp. 28-37.
Rayleigh, "On copying diffraction gratings and some phenomena connected therewith," Philos. Mag. vol. 11 (1881), pp. 196-205.
Renaud et al., "Probing surface and interface morphology with Grazing Incidence Small Angle X-ray Scattering," Surface Science Reports, vol. 64:8 (2009), pp. 255-380.
Riege, "Electron Emission from Ferroelectrics—A Review", CERN Report CERN AT/93-18 (CERN, Geneva, Switzerland, Jul. 1993).
Röntgen, "Ueber eine neue Art von Strahlen (Wuzburg Verlag, Warzburg, Germany, 1896) also, in English, On a New Kind of Rays," Nature vol. 53 (Jan. 23 1896). pp. 274-276.
Rovezzi, "Study of the local order around magnetic impurities in semiconductors for spintronics." PhD Dissertation, Condensed Matter, Université Joseph-Fourier-Grenoble I, 2009, English <tel-00442852>.
Rutishauser, "X-ray grating interferometry for imaging and metrology," 2003, Eth Zurich, Diss. ETH No. 20939.
Sato et al., Two-dimensional gratings-based phase-contrast imaging using a conventional x-ray tube, 2011, Optics Letters, vol. 36, No. 18, pp. 3551-3553.
Scherer et al., "Bi-Directional X-Ray Phase-Contrast Mammography," PLoS One, vol. 9, Issue 5 (May 2014) e93502.
Scholz, "X-ray Tubes and Monochromators," Technical Workshop EPIV, Universität Würzburg (2007); 41 slides, 2007.
Scholze et al., "X-ray Detectors and XRF Detection Channels," Ch. 4 of "Handbook of Practical X-Ray Fluorescence Analysis," B. Beckhoff et al., eds. (Springer, Berlin Heidelberg, Germay, 2006), pp. 85-198.
Sebert, "Flat-panel detectors:how much better are they?" Pediatr. Radiol. vol. 36 (Suppl 2), (2006), pp. 173-181.
Shen, "Polarizing Crystal Optics," Ch. 25 of "Handbook of Optics vol. III, 2nd Ed.," (McGraw Hill, New York, 2001).
Shields et al., "Overview of Polycapillary X-ray Optics," Powder Diffraction, vol. 17(2) (Jun. 2002), pp. 70-80.
Shimura et al., "Hard x-ray phase contrast imaging using a tabletop Talbot-Lau interferometer with multiline embedded x-ray targets", Opt. Lett. vol. 38(2) (2013), pp. 157-159.
Siddons, "Crystal Monochromators and Bent Crystals," Ch. 22 of "Handbook of Optics vol. III, 2nd Ed.," (McGraw Hill, New York, 2001).
Smith, "Fundamentals of Digital Mammography:Physics, Technology and Practical Considerations," Publication R-BI-016 (Hologic, Inc., Bedford, MA, Mar. 2005).
Snigirev et al., "Hard X-Ray Microoptics," Ch. 17 of "Modern Developments in X-Ray and Neutron Optics," A. Erko et al., eds (Springer, Berlin, Germany, 2008), pp. 255-285.
Sparks Jr., "X-ray Fluorescence Microprobe for Chemical Analysis," in Synchrotron Radiation Research, H. Winick & S. Doniach, eds. (Plenum Press, New York, NY 1980), pp. 459-512.
Spiller, "Multilayers," Ch. 24 of "Handbook of Optics vol. III, 2nd Ed.," (McGraw Hill, New York, 2001).
Stampanoni et al., "The First Analysis and Clinical Evaluation of Native Breast Tissue Using Differential Phase-Contrast Mammography," Investigative Radiology, vol. 46, pp. 801-806. pub Dec. 2011.
Strüder et al., "Silicon Drift Detectors for X-ray Imaging," Presentation at Detector Workshop on Synchrotron Radiation Instrumentation, 54 slides, (Argonne Nat'l Lab, Argonne, IL Dec. 8, 2005), available at: <http://www.aps.anl.gov/News/Conferences/2005/Synchrotron_Radiation_Instrumentation/Presentations/Strueder.pdf>.
Strüder et al., "X-Ray Detectors," Ch. 4 of "X-ray Spectrometry: Recent Technological Advances," K. Tsuji et al. eds. (John Wiley & Sons, Ltd. Chichester, West Sussex, UK, 2004), pp. 63-131.
Suzuki et al., "Hard X-ray Imaging Microscopy using X-ray Guide Tube as Beam Condenser for Field Illumination," J. Phys.: Conf. Ser. vol. 463 (2013): 012028.
Suzuki, "Development of the DIGITEX Safire Cardiac System Equipped with Direct conversion Flat Panel Detector," Digital Angio Technical Report (Shimadzu Corp., Kyoto, Japan, no date, published-2004 with product release).

(56) References Cited

OTHER PUBLICATIONS

Takahama, "RADspeed safire Digital General Radiography System Equipped with New Direct-Conversion FPD," Medical Now, No. 62 (2007).
Takeda et al., "Differential Phase X-ray Imaging Microscopy with X-ray Talbot Interferometer" Appl. Phys. Express vol. 1 (2008) 117002.
Takeda et al., "X-Ray Phase Imaging with Single Phase Grating", Jpn. J. Appl. Phys. vol. 46 (2007), pp. L89-L91.
Takeda et al., "In vivo physiological saline-infused hepatic vessel imaging using a two-crystal-interferometer-based phase-contrast X-ray technique", J. Synchrotron Radiation vol. 19 (2012), pp. 252-256.
Talbot, "Facts relating to optical science No. IV," Philos. Mag. vol. 9 (1836), pp. 401-407.
Tanaka et al., "Cadaveric and in vivo human joint imaging based on differential phase contrast by X-ray Talbot-Lau interferometry", Z. Med. Phys. vol. 23 (2013), pp. 222-227.
Tang et al., "Micro-computed tomography (Micro-CT): a novel appraoch for intraoperative breast cancer specimen imaging," Breast Cancer Res. Treat. vol. 139, pp. 311-316 (2013).
Taniguchi et al., "Diamond nanoimprint lithography," Nanotechnology, vol. 13 (2002) pp. 592-596.
Touzelbaev et al., "Applications of micron-scale passive diamond layers for the integrated circuits and microelectromechanical systems industries," Diamond and Rel. Mat'ls, vol. 7 (1998) pp. 1-14.
Tsuji et al., "X-Ray Spectrometry: Recent Technological Acvances," John Wiley & Sons Ltd. Chichester, West Susses, UK 2004), Chapters 1-7.
Udagawa, "An Introduction to In-House EXAFS Facilities," The Rigaku Journal, vol. 6, (1) (1989), pp. 20-27.
Udagawa, "An Introduction to X-ray Absorption Fine Structure," The Rigaku Journal, vol. 11(2)(1994), pp. 30-39.
Uehara et al., "Effectiveness of X-ray grating interferometry for non-destructive inspection of packaged devices", J. Appl. Phys. vol. 114 (2013), 134901.
Vogt, "X-ray Fluorescence Microscopy: A Tool for Biology, Life Science and Nanomedicine," Presentation on May 16, 2012 at James Madison Univ., Harrisonburg, VA (31 slides), 2012.
Wan et al.,"Fabrication of Multiple Slit Using Stacked-Sliced Method for Hard X-ray Talbot-Lau Interferometer", Jpn. J. Appl. Phys. vol. 47 (2008), pp. 7412-7414.
Wang et al., "Advantages of intermediate X-ray energies in Zernicke phase constrast X-ray microscopy," Biotech. Adv., vol. 31 (2013) pp. 387-392.
Wang et al., "Non-invasive classification of microcalcifications with phase-contrast X-ray mammography," Nature Comm. vol. 5:3797, pp. 1-9 (2014).
Wang, On the single-photon-counting (SPC) modes of imaging using an XFEL source, presented at IWorld (2015).
Wang et al., "Precise patterning of diamond films for MEMS application" Journal of Materials Processing Technology vol. 127 (2002), pp. 230-233.
Weitkamp et al., "Design aspects of X-ray grating interferometry," in International Workshop on X-ray and Neutron Phase Imaging with Gratings AIP Conf. Proc. vol. 1466, (2012), pp. 84-89.
Weitkamp et al., "Hard X-ray phase imaging and tomography with a grating interferometer," Proc. SPIE vol. 5535, (2004), pp. 137-142.
Weitkamp et al., "X-ray wavefront diagnostics with Talbot interferometers," International Workshop on X-Ray Diagnostics and Scientific Application of the European XFEL, Ryn, Poland, (2010), 36 slides.
Weitkamp et al., Tomography with grating interferometers at low-brilliance sources, 2006, SPIE, vol. 6318, pp. 0S-1 to 0S-10.
Weitkamp et al., "X-ray phase imaging with a grating interferometer," Opt. Express vol. 13(16), (2005), pp. 6296-6304.
Weitkamp et al., "X-ray wavefront analysis and optics characterization with a grating interferometer," Appl. Phys. Lett. vol. 86, (2005), 054101.
Wen et al., "Fourier X-ray Scattering Radiography Yields Bone Structural Information," Radiology, vol. 251 (2009) pp. 910-918.
Wen et al., "Single-shot x-ray differential phase-contrast and diffraction imaging using two-dimensional transmission gratings," Op. Lett. vol. 35, No. 12, (2010) pp. 1932-1934.
Wobrauschek et al., "Energy Dispersive, X-Ray Fluorescence Analysis," Encyclopedia of Analytical Chemistry, R.A. Meyers, Ed. (Wiley 2010).
Wobrauschek et al., "Micro XRF of light elements using a polycapillary lens and an ultra-thin window Silicon Drift Detector inside a vacuum chamber," 2005, International Centre for Diffraction Data 2005, Advances in X-ray Analysis, vol. 48, pp. 229-235.
Wolter, "Spiegelsysteme streifenden Einfalls als abbildende Optiken fur Rontgenstrahlen" [Grazing Incidence Reflector Systems as Imaging Optics for X-rays] Annalen der Physik vol. 445, Issue 1-2 (1952), pp. 94-114.
X-ray-Optics.de Website, http://www.x-ray-optics.de/, accessed Feb. 13, 2016.
Yakimchuk et al., "Ellipsoidal Concentrators for Laboratory X-ray Sources: Analytical approaches for optimization," Mar. 22, 2013, Crystallography Reports, vol. 58, No. 2, pp. 355-364.
Yamamoto, "Fundamental physics of vacuum electron sources", Reports on Progress in Physics vol. 69, (2006), pp. 181-232.
Yanagihara et al., "X-Ray Optics," Ch. 3 of "X-ray Spectrometry: Recent Technological Advances," K. Tsuji et al. eds. (John Wiley & Sons, Ltd. Chichester, West Sussex, UK, 2004), pp. 63-131.
Yang et al., "Analysis of Intrinsic Stress in Diamond Films by X-ray Diffraction," Advances in X-ray Analysis, vol. 43 (2000), pp. 151-156.
Yashiro et al., "Distribution of unresolvable anisotropic microstructures revealed in visibility-contrast images using x-ray Talbot interferometry", Phys. Rev. B vol. 84 (2011), 094106.
Yashiro et al., "Hard x-ray phase-imaging microscopy using the self-imaging phenomenon of a transmission grating", Phys. Rev. A vol. 82 (2010), 043822.
Yashiro et al., "Theoretical Aspect of X-ray Phase Microscopy with Transmission Gratings" in International Workshop on X-ray and Neutron Phase Imaging with Gratings, AIP Conf. Proc. vol. 1466, (2012), pp. 144-149.
Yashiro et al., "X-ray Phase Imaging and Tomography Using a Fresnel Zone Plate and a Transmission Grating", in "The 10th International Conference on X-ray Microscopy Radiation Instrumentation", AIP Conf. Proc. vol. 1365 (2011) pp. 317-320.
Yashiro et al., "Efficiency of capturing a phase image using cone-beam x-ray Talbot interferometry", J. Opt. Soc. Am. A vol. 25 (2008), pp. 2025-2039.
Yashiro et al., "On the origin of visibility contrast in x-ray Talbot interferometry", Opt. Express (2010), pp. 16890-16901.
Yashiro et al., "Optimal Design of Transmission Grating for X-ray Talbot Interferometer", Advances in X-ray Analysis vol. 49(3) (2006), pp. 375-379.
Yashiro et al., "X-ray Phase Imaging Microscopy using a Fresnel Zone Plate and a Transmission Grating", in The 10th International Conference on Synchrotron Radiation Instrumentation, AIP Conf. Proc. vol. 1234 (2010), pp. 473-476.
Yashiro et. al., "Hard-X-Ray Phase-Difference Microscopy Using a Fresnel Zone Plate and a Transmission Grating", Phys. Rev. Lett. vol. 103 (2009), 180801.
Yu et al., "Morphology and Microstructure of Tungsten Films by Magnetron Sputtering," Mat. Sci. Forum, vol. 913, pp. 416-423 (2018).
Zanette et al., "Two-Dimensional X-Ray Grating interferometer," Phys. Rev. Lett. vol. 105 (2010) pp. 248102-1 248102-4.
Zeng et al., "Ellipsoidal and parabolic glass capillaries as condensers for x-ray microscopes," Appl. Opt. vol. 47 (May 2008), pp. 2376-2381.
Zeng et al., "Glass Monocapillary X-ray Optics and Their Applications in X-Ray Microscopy," X-ray Optics and Microanalysis: Proceedings of the 20th International Congress, AIP Conf. Proc. vol. 1221, (2010), pp. 41-47.

(56) References Cited

OTHER PUBLICATIONS

Zhang et al., "Fabrication of Diamond Microstructures by Using Dry and Wet Etching Methods", Plasma Science and Technology vol. 15(6) (Jun. 2013), pp. 552-554.

\* cited by examiner

METHOD AND APPARATUS FOR X-RAY MICROSCOPY

CROSS-REFERENCE TO RELATED APPLICATIONS

This Patent Application is a continuation-in-part of U.S. patent application Ser. No. 15/173,711, filed Jun. 5, 2016 and entitled "X-RAY TECHNIQUES USING STRUCTURED ILLUMINATION", which claims the benefit of U.S. Provisional Patent Application Nos. 62/171,377, filed on Jun. 5, 2015 and entitled "X-RAY TECHNIQUES USING STRUCTURED ILLUMINATION", and 62/343,594, filed on May 31, 2016 and entitled "X-RAY MICRODIFFRACTION WITH STRUCTURED ILLUMINATION FOR STRAIN MEASUREMENT IN NANOELECTRONICS", all of which are incorporated herein by reference in their entirety.

Application Ser. No. 15/173,711 additionally is a continuation-in-part of U.S. patent application Ser. No. 14/712,917, filed May 15, 2015 and entitled "X-RAY METHOD FOR MEASUREMENT, CHARACTERIZATION, AND ANALYSIS OF PERIODIC STRUCTURES", which in turn is a continuation-in-part of U.S. patent application Ser. No. 14/700,137, filed Apr. 29, 2015 and entitled "X-RAY INTERFEROMETRIC IMAGING SYSTEM", both of which are incorporated herein by reference in their entirety. The present Application additionally claims the benefit of U.S. Provisional Patent Application Nos. 62/401,164, filed Sep. 28, 2016 and entitled "X-RAY MEASUREMENT TECHNIQUES USING MULTIPLE MICRO-BEAMS", 62/429,587, filed Dec. 2, 2016 and entitled "METHOD FOR TALBOT X-RAY MICROSCOPY"; 62/429,760, filed Dec. 3, 2016 and entitled "MATERIAL MEASUREMENT TECHNIQUES USING MULTIPLE X-RAY MICRO-BEAMS", and 62/485,916, filed Apr. 15, 2017 and entitled "TALBOT X-RAY MICROSCOPE", all of which are hereby incorporated by reference in their entirety.

FIELD OF THE INVENTION

The embodiments of the invention disclosed herein relate to microscopy systems using x-rays, and, in particular, measurement, characterization and analysis systems using a system of periodic micro-beams to illuminate an object to determine various structural and chemical properties of the object.

BACKGROUND OF THE INVENTION

Conventional x-ray microscopes that utilize imaging optics are generally limited by the resolution of the x-ray optics (e.g. zone plates) and/or the resolution of the pixel size of the detector. For projection-based systems, the resolution is limited by the size of the x-ray source and the finite pixel size of the detector. Although some commercial x-ray microscope systems utilizing zone plates have a resolution of less than 100 nm, such systems have an extremely limited field of view. Projection based x-ray microscopes do provide reasonable field of view with resolution better than 1 micron, but the acquisition times for reasonable signal-to-noise ratio tend to be very long, rendering the technique practically useless for many applications. Therefore, x-ray microscopy with resolution smaller than 1 micron while also having a large field-of-view has difficulty producing images with an integration time short enough to make the technique practical.

There is therefore a need for high-resolution microscopy systems that can provide both high resolution and a large field of view.

BRIEF SUMMARY OF THE INVENTION

This disclosure presents systems for x-ray microscopy using an array of micro-beams having a micro- or nano-scale beam intensity profile to provide selective illumination of micro- or nano-scale regions of an object. An array detector is positioned such that each pixel of the detector only detects x-rays corresponding to a single micro-beam, allowing the signal arising from the x-ray detector to be identified with the specific, limited micro- or nano-scale regions illuminated. Sampled transmission images of the object under examination at a micron- or nano-scale can therefore be generated while using a detector with pixels having a larger size and scale.

In some embodiments, the micro- or nano-scale beams may be provided by producing a set of Talbot interference fringes, which can create a set of fine x-ray micro-beams propagating in space. In some embodiments, the array of micro- or nano-beams may be provided by a conventional x-ray source and an array of x-ray imaging elements (e.g. x-ray lenses).

In some embodiments, both the detector and the object are placed within the same defined "depth-of-focus" (DOF) range of a set of Talbot anti-nodes. In some embodiments, the object is positioned on a mount that allows translation in the x- and y-directions perpendicular to the direction of x-ray beam propagation, allowing a "scanned" transmission image on a microscopic scale to be assembled. In some embodiments, the object is positioned on a mount that allows rotation about an axis at a predetermined angle to the direction of x-ray beam propagation, allowing the collection of data on a microscopic scale to be used for laminographic or tomographic image reconstruction.

In some embodiments, additional masking layers may be inserted in the beam path to block a selected number of the micro-beams, allowing the use of less expensive detectors with larger pixel sizes for the remaining micro-beams. In some embodiments, the use of a masking layer also allows the use of a detector with enhanced detection efficiency for the remaining micro-beams. Such masking layers may be placed in front of the object to be examined, between the object and the detector, or be designed as part of the detector structure itself.

Figure 1A:
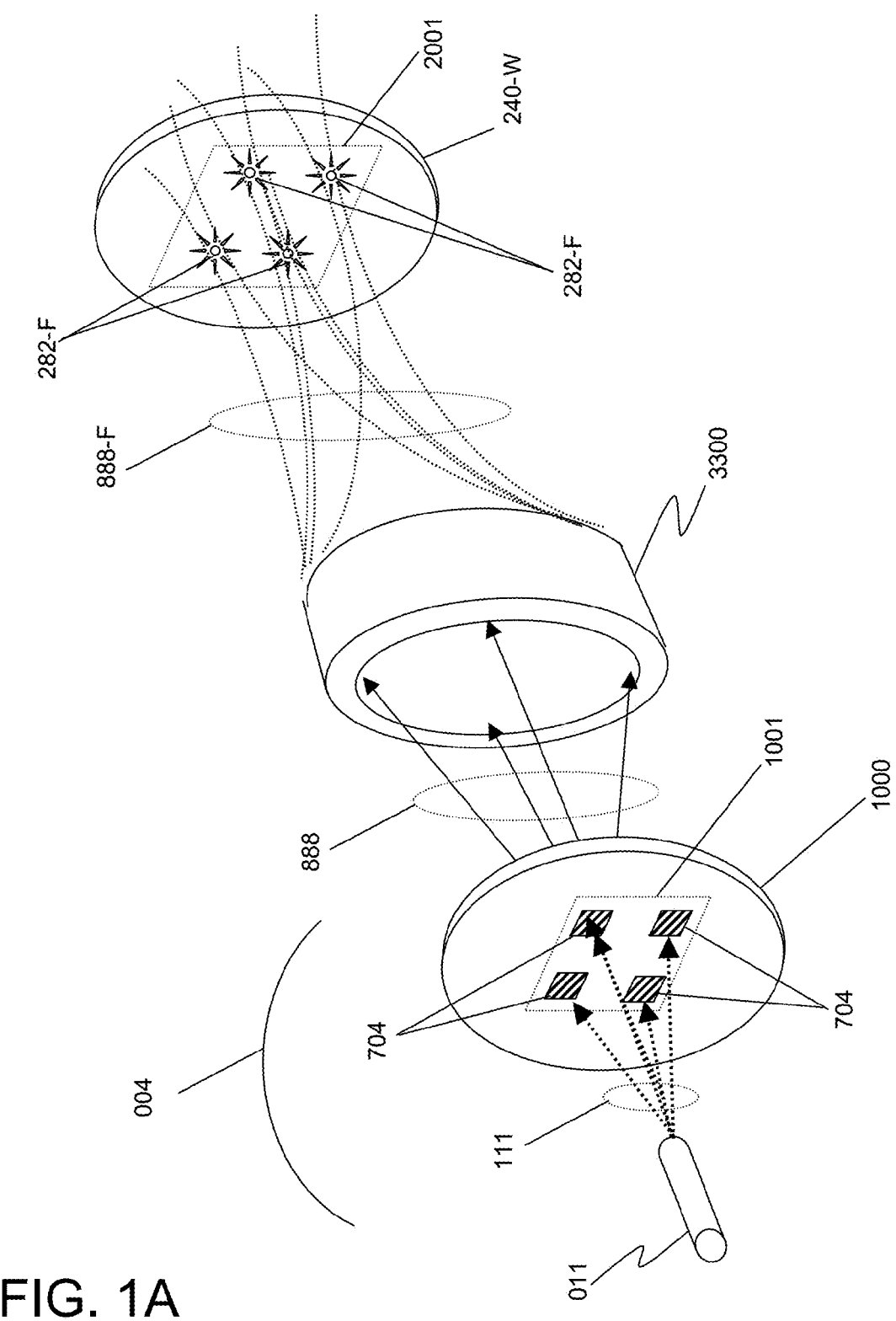
FIG. 1A illustrates a schematic view of an x-ray imaging system providing an array of micro-beams as may be used in some embodiments of the invention.

Note: The illustrations in the Drawings disclosed in this Application are meant to illustrate the principle of the invention and its function only, and are not shown to scale. Please refer to the descriptions in the text of the Specification for any specific details regarding the dimensions of the elements of the various embodiments (e.g. x-ray source dimension a, grating periods $p_0$, $p_1$, $p_2$, etc.) and relationships between them.

DETAILED DESCRIPTION OF EMBODIMENTS OF THE INVENTION

1. Imaging with Arrays of Micro-Beams.

FIG. 1A illustrates a simple embodiment of the invention comprising the formation of an array of micro-beams. An arrayed source 004 comprising an electron emitter 011 that produces electrons 111 that bombard a target 1000 comprising a region 1001 containing structures of x-ray generating materials 704. In this illustration, four material structures 704 that are sub-sources of the x-rays are shown arranged in an array, although the target may comprise any number of source points and, of these source points, any number may be used.

The four structures of x-ray generating materials 704, when bombarded by electrons 111, produce x-rays 888 that propagate away from the target. In the embodiment as illustrated, these x-rays 888 enter an x-ray optical system 3300 that converts the waveform into focused x-rays 888-F that form an image of the x-ray array region 1001 at a predetermined region 2001 in space. Such an optical system may be a simple x-ray focusing element, such as a capillary with an inner quadric surface, or a more complex multi-element imaging system. In this case, with four x-ray source points, the image will comprise four spots 282-F, each having a diameter related to the size of the original x-ray generating source point and the magnification of the optical system 3300, and having a length defined by the depth-of-focus of the optical system, generally related to the x-ray wavelength and the square of the numerical aperture (NA) of the x-ray optical system.

Figure 1B:
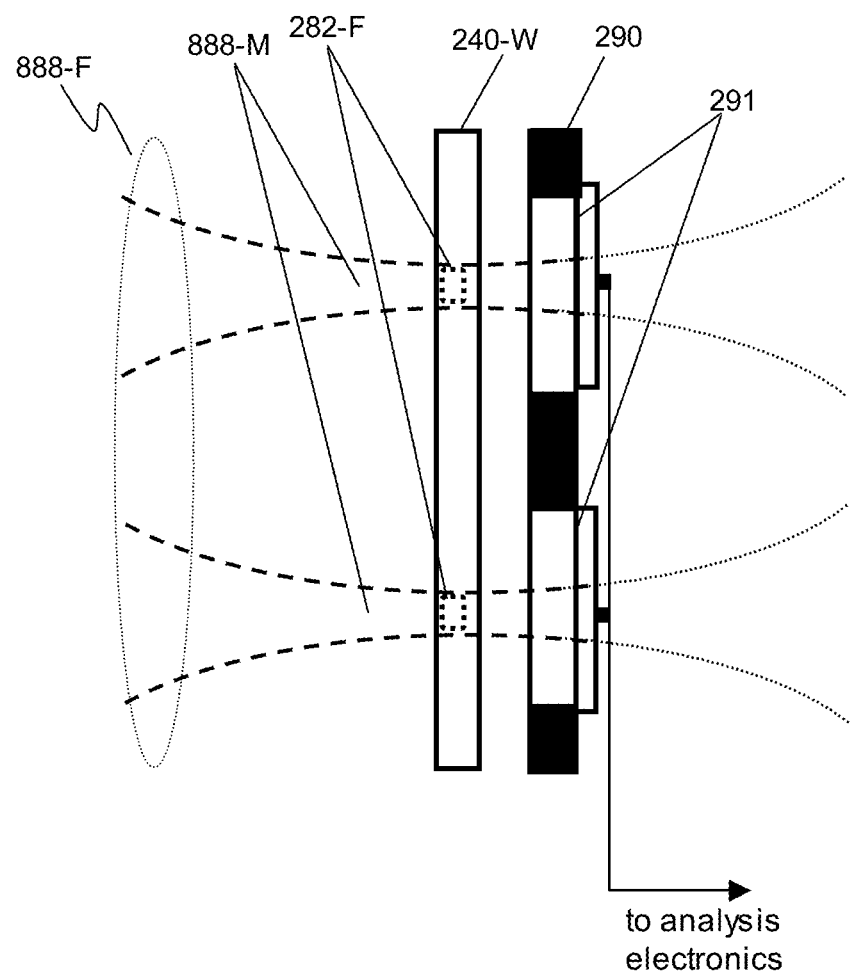
FIG. 1B illustrates a cross-section view of the x-ray imaging system of FIG. 1A.

FIG. 1B illustrates a cross section view of the converging x-ray field 888-F, showing the formation of micro-beams 888-M at this point in space. By placing an object to be examined 240-W at this position in space, the micro-beams 888-M will illuminate the object at specific spatially defined points 282-F, having a diameter of the micro-beam 888-M, which is determined by the size of the original x-ray source point, the x-ray wavelength, and the properties (NA, Magnification) of the optical system 3300. By placing an x-ray detector 290 having pixels 291 with a pitch matched to the pitch of the micro-beams 888-M and a position within the depth-of-focus, the x-rays detected by each pixel are therefore provided by only one micro-beam. The entire signal generated therefore represents the x-ray transmission of only the much smaller illumination spot 282-F. As an example, for a micro-beam diameter of 1 micron, a detector pixel as large as 25 microns may provide information about only the single micron diameter spot when the pitch between micro-beams is larger or equal to the detector pixel pitch.

Such a system will produce a set of arrayed points from the detector representing sample points at each micro-beam. For some applications, this sampling of the x-ray transmission through an object may be sufficient. In other cases, the relative position of the object and the array of micro-beams may be scanned in x- and y-dimensions to produce a scanned "map" of the object. Since each data point represents the information produced by a smaller micro-beam, a high-resolution image using a lower-resolution pixel detector can be achieved. Such scanning techniques for structured illumination have been additionally described in co-pending U.S. patent application Ser. No. 15/173,711 entitled X-RAY TECHNIQUES USING STRUCTURED ILLUMINATION, filed Jun. 5, 2016, and in the U.S. Provisional Patent Application 62/401,164 entitled X-RAY MEASUREMENT TECHNIQUES USING MULTIPLE MICRO-BEAMS, which are both hereby incorporated by reference in their entirety.

The above example presents one way to form an array of micro-beams using an arrayed x-ray source and imaging optics. Although functional for demonstrating the principle, such an approach is limited by the field of view of the x-ray optical system, and various embodiments of the invention may use any number of techniques that create an array of micro- or nano-scale x-ray beams used for illuminating an object.

2. Talbot Fringes as an Array of Micro-Beams.

Talbot interference fringes can be a highly efficient method of directing x-rays into an effective array of micro-beams. The effective lateral dimension of the Talbot anti-nodes (typically defined as regions of constructive interference) can, using the appropriate beam-splitting grating to establish the fringes, be made to be very small, as small as 20 nm, while the overall interference field of the Talbot interference pattern can cover an area of several cm². A Talbot interference pattern, when used to illuminate an object under investigation in transmission, provides an array of discrete micro- or nano-probes that can be detected and analyzed using an array detector.

As was described above for the imaging system, when the detector is selected to have a pixel size that corresponds to the pitch of the Talbot fringes, and both the object and the detector are placed within the effective "depth-of-focus" of the Talbot fringes, each pixel is detecting transmitted x-rays from a single one of the micro-beams. This allows the advantages of decoupling the illumination spot size and the pixel dimension to be achieved, and the Talbot interference phenomenon allows an array of effective micro-beams to be formed over a large area.

Talbot interference fringes using a structured x-ray source have been the subject of other Patent Applications by the inventors of the present Application, including Ser. Nos. U.S. Ser. No. 14/527,523, U.S. Ser. Nos. 14/700,137, 14/712,917, U.S. Ser. Nos. 14/943,445, and 15/173,711, all of which are hereby incorporated by reference.

Talbot interference has been used for lower resolution imaging, and in particular, for phase contrast imaging, for some time (See, for example, Atsushi Momose, Wataru Yashiro, and Yoshihiro Takeda, "X-Ray Phase Imaging with Talbot Interferometry", in *Biomedical Mathematics: Promising Directions in Imaging, Therapy Planning, and Inverse Problems*, Y. Censor, M. Jiang and G. Wang, Editors, (Medical Physics Publishing, Madison, Wis., 2009), pp. 281-320 and references therein). Such systems typically use a diffractive grating (often a phase-shifting grating) to produce the Talbot interference pattern, and then analyze the resulting pattern with a second grating and/or an array x-ray detector.

Figure 2:
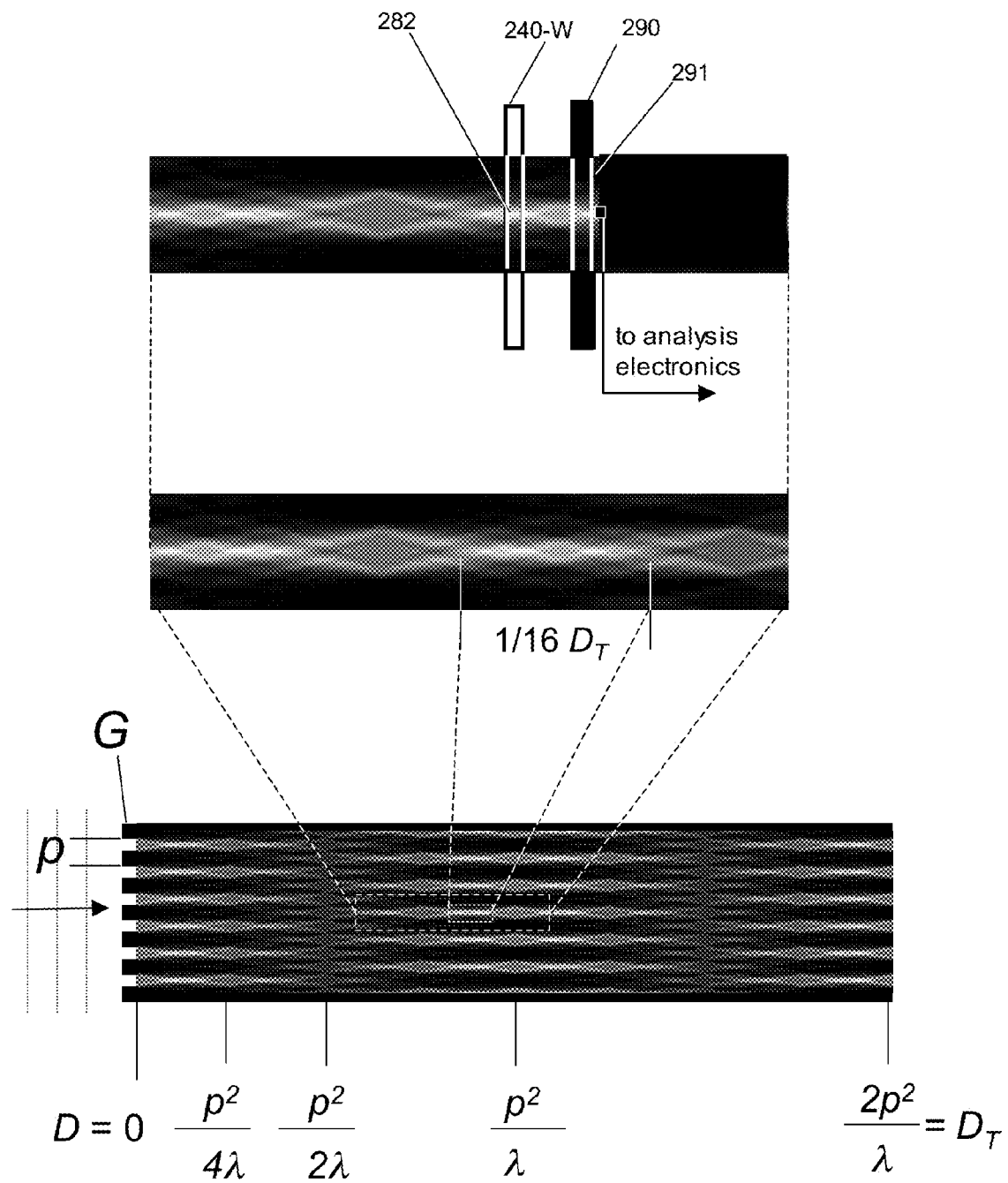
FIG. 2 illustrates the use of a Talbot interference fringe pattern from a 1:1 duty cycle absorption grating G used as an array of micro-beams for an embodiment of the invention.

FIG. 2 illustrates a cross section of representative Talbot interference pattern generated by an absorption grating G having a 50/50 duty cycle with a pitch p when illuminated by a plane wave. The fringes in this illustration are adapted from FIG. 19(a) of section 9.3, "Phase Contrast Imaging", in Elements of Modern X-ray Physics, Second Edition", Jens Als-Nielsen & Des McMorrow (John Wiley & Sons Ltd, Chichester, West Sussex, UK, 2011). This has been presented for illustrative purposes only; no restriction or limitation of the scope of the invention should be implied by the use of this particular illustration.

As shown in FIG. 2, interference fringes are generated behind the absorption grating. Self-images of the grating with pitch p and a 50/50 duty cycle occur at the Talbot distances $D_T$, given by $$D_T = n\frac{2p^2}{\lambda} \quad \text{[Eqn. 1]}$$

where p is the period of the beam splitting grating, n is an integer, and $\lambda$ is the x-ray wavelength. The darker regions, where destructive interference occurs, are generally called "nodes" of the interference pattern, whereas the bright regions of constructive interference are generally called "anti-nodes" of the interference pattern.

As an x-ray illuminator, the Talbot interference pattern can, with the suitable selection of a beam-splitting grating with micron-scale features, produce an interference pattern of bright anti-nodes with a corresponding micron-scale for the anti-node dimension. For x-rays with an energy of 24.8 keV, the wavelength is $\lambda$=0.05 nm, so for an absorption grating with a 50/50 duty cycle and a 1 micron pitch, the first (n=1) Talbot distance is $D_T$=4 cm. Therefore, the scales for the x- and y-directions of the fringes in the illustration of FIG. 2 are quite different, with micron-scale dimensions perpendicular to the direction of propagation shown, but centimeter-scale dimensions used along the direction of propagation.

Fringe patterns at various fractional Talbot distances may be inverted in bright and dark fringes, and the size of the bright (anti-node) fringes at various fractional Talbot distances may actually be smaller than the size of the original grating features. These anti-nodes may therefore serve as the multiple micro-beams used for illuminating an object.

When Talbot interference phenomena is utilized, there are specific predetermined regions within the Talbot interference pattern over which a bright fringe maintains a certain intensity micro-beam profile. Such regions (several of which can be seen in the example of FIG. 2) are comparable to the "depth-of-focus" range of more conventional imaging systems, and for a Talbot pattern arranged as an array, these corresponding predetermined regions will form an array of micro-beams. The region of the "depth-of-focus" may be also defined relative to the Talbot Distance $D_T$. For example, in the illustration of FIG. 2, a region of an anti-node forming a micro-beam is illustrated as having a length of approximately 1/16 $D_T$. Placing the object 240-W and the detector 290 having a pixel 291 within this predetermined anti-node region allows the signal from a much larger pixel 291 to represent the transmission of the much smaller region 282 where the anti-node illuminates the object.

The pattern shown in FIG. 2 represents a non-divergent Talbot interference pattern, but in some embodiments, the Talbot pattern will be comprise x-rays which are diverging from a common x-ray source.

In many embodiments, the beam splitting diffraction grating used to form the Talbot pattern may be a phase grating of low absorption but producing considerable x-ray phase shift of either $\pi/2$ or $\pi$ radians, or some other specified or predetermined value such as an integer multiple of $\pi/2$. These gratings may also comprise one-dimensional or two-dimensional grating patterns.

As noted above, depending on the dimensions of the beam-splitting grating, these probe sizes can be as small as 20 nm with the appropriate selection of a suitably fine beam-splitting grating. As in the previously mentioned co-pending US Patent Applications and US Provisional Patent Applications, scanning the object in x- and y-dimensions allows the micro- or nano-scale probing beams to be moved over the object so that a complete high resolution "map" of the transmission of the object may be obtained with a relatively lower resolution detector.

Figure 3A:
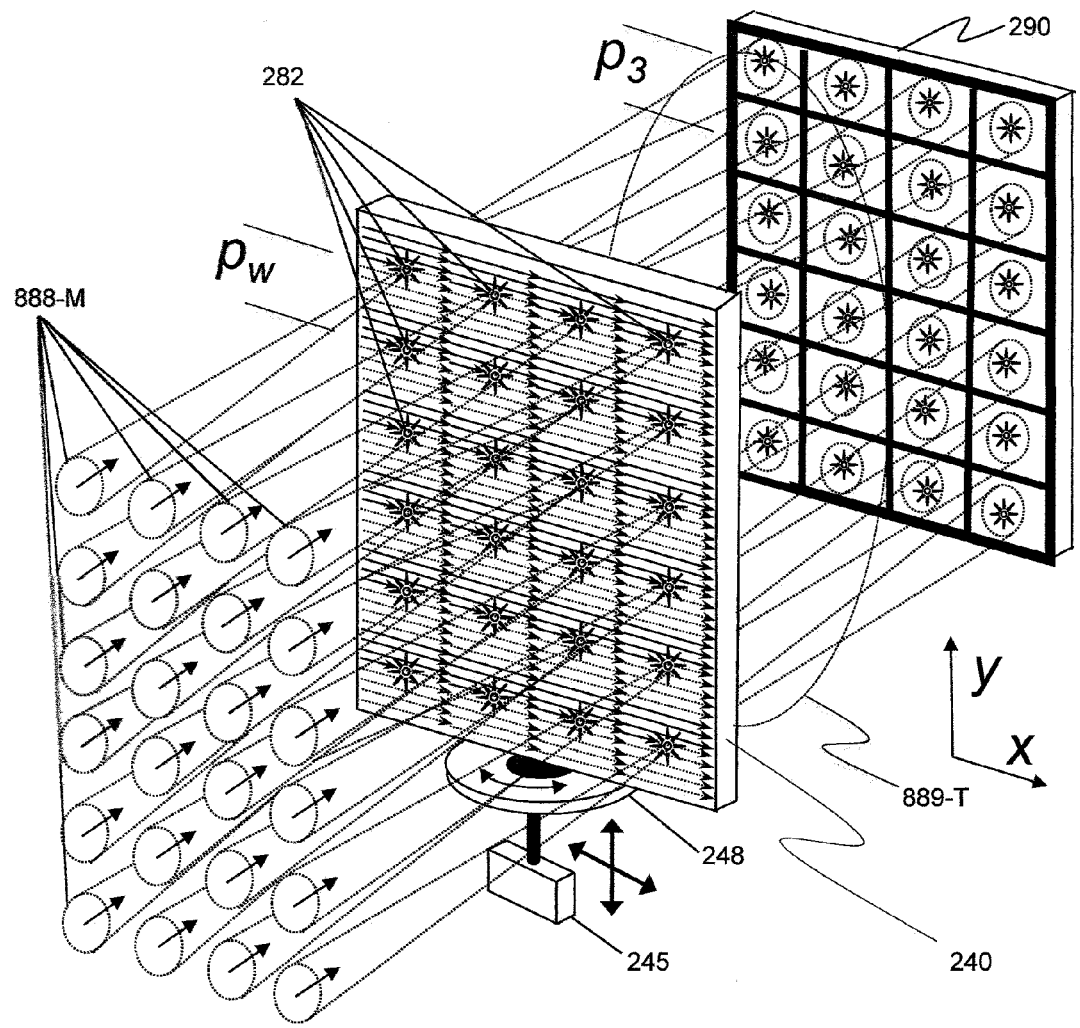
FIG. 3A illustrates a schematic view of the micro-beams, object, and detector as used in some embodiments of the invention.
Figure 3B:
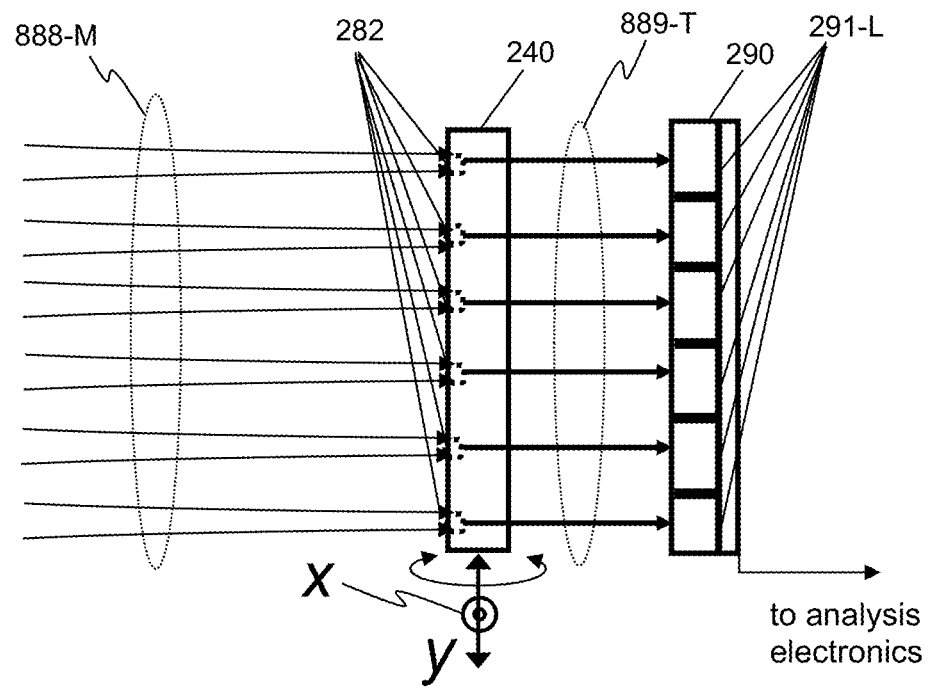
FIG. 3B illustrates a schematic cross-section view of the micro-beams, object, and detector of the embodiment of FIG. 3A.
Figure 3C:
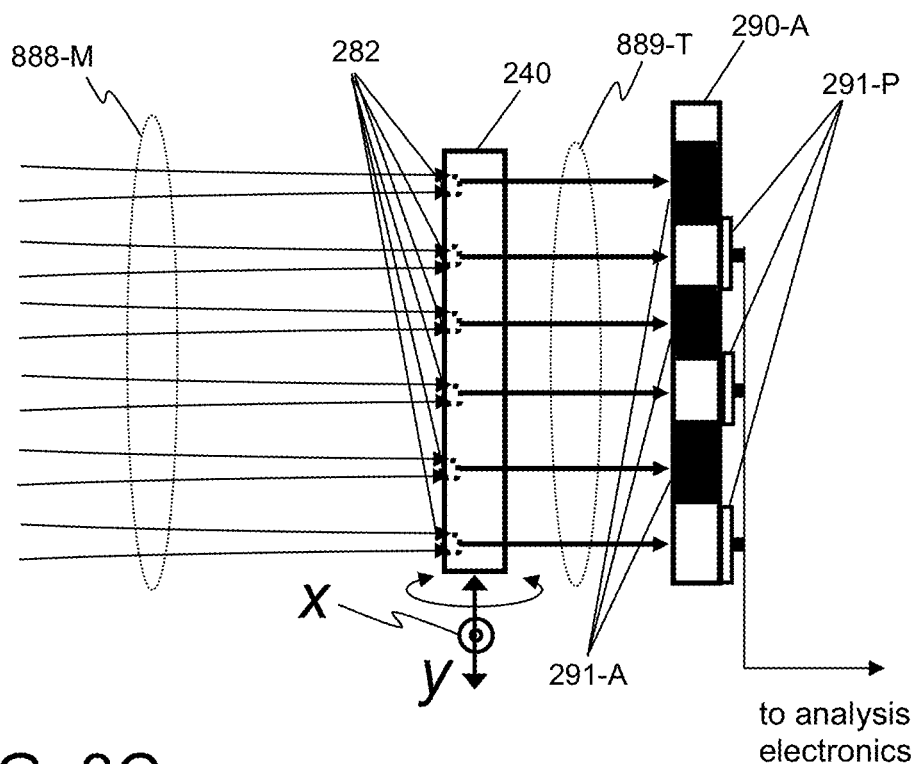
FIG. 3C illustrates a schematic cross-section view of the micro-beams, object, and detector of the variation of the embodiment of FIGS. 3A and 3B, in which portions of the detector array are active elements and other portions are inactive.

A schematic of an embodiment as may be used with any micro-beam forming system is illustrated in FIGS. 3A and 3B. When an array of micro beams 888-M having a pitch $p_w$ is formed, the object 240 to be examined is illuminated at an array of discrete interaction locations 282 also having pitch $p_w$. As illustrated, the x-ray beam pitch in x- and y- is the same and equal to $p_w$, but other embodiments in which the pitch in x- and y-dimensions are different may also be used. Differences in pitch may also be due to divergence properties of the Talbot pattern. FIG. 3C illustrates the use of a detector 290-A, in which active pixels 291-P and inactive areas 291-A are both present in the detector to select only certain micro-beams for detection.

The position of the object can be scanned in x- and y-dimensions perpendicular to the direction of propagation of the micro-beams using a position controller 245, and the transmitted x-rays 888-T resulting from the interaction of the micro-beams and the object can be detected by an array detector 290.

In this embodiment, the array detector 290 has a pitch $p_3$ which, in this example, is also equal to $p_w$. This means that the detector will be aligned such that each pixel of the array detector will be positioned to collect only x-rays corresponding to a single micro-beam. By pairing the use of multiple micro-beams with a detector having a pixel pitch matched to the pitch of the micro-beams, and also aligned so that each pixel detects x-rays from only the interaction of a single micro-beam at a given position on the object, the equivalent of $10^2$ to $10^4$ parallel micro-beam detection systems can be created. Other detectors with smaller pixels, in which multiple pixels detect the x-rays of a single micro-beam, may also be used, as long as all transmission x-rays detected by each pixel have their origin from a single micro-beam.

As before, the object can then be scanned in x- and y-coordinates. This produces "maps" in parallel of the properties of the object, but the range of motion can be reduced to only correspond to the pitch of the micro-beams (although some overlap between scanned areas may be appropriate to provide a relative calibration).

The "maps" generated by each pixel may then be stitched together digitally to produce a large-scale "macro-map" of the object properties, while reducing the corresponding data collection time by a factor related to the number of micro-beams (e.g. up to a factor of $10^4$).

To achieve some degree of tomographic analysis, limited angle adjustment of the object may also be added to the motion protocol, as long as the interaction of x-rays with the region of interest in the object as well as the corresponding detector pixel both remain within a region defined by the depth-of-focus for all of the multiple micro-beams. A rotation stage 248 to achieve this purpose has also been illustrated as part of the mount for the object 240 in FIG. 3A. In some embodiments, a 5-axis mount, or a goniometer, may be used to allow translation and rotation from the same mounting system. In some embodiments, the object may remain stationary, and mechanism forming the Talbot fringes (along with the aligned detector) may be translated or rotated relative to the object.

Figure 4:
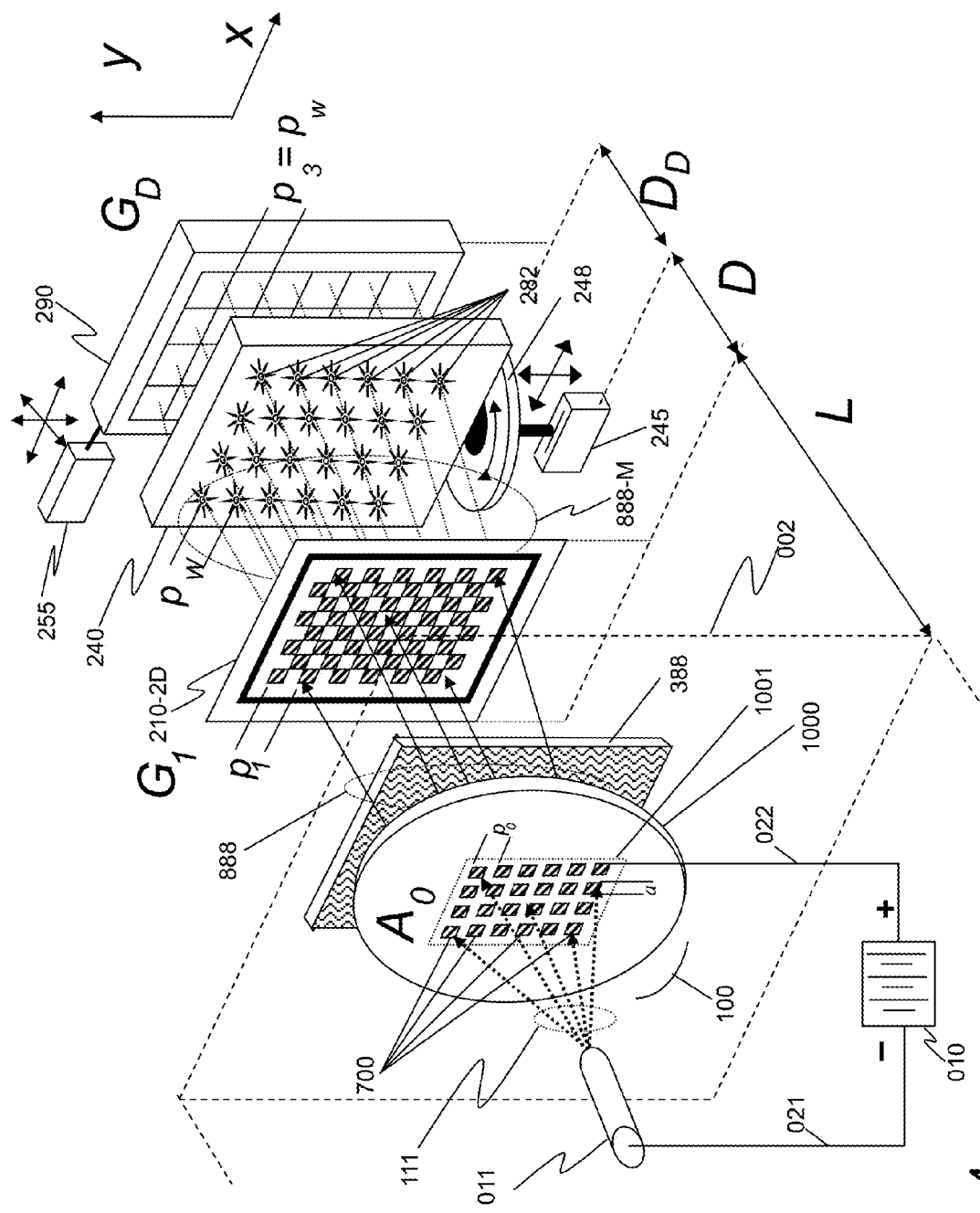
FIG. 4 illustrates a schematic view of a microscope system using a beam-splitting grating $G_1$ to generate micro-beams from Talbot interference fringes.

Although the periodic Talbot pattern may be formed by any of the means as described in the previously cited references and Patent Applications, one innovation that has been shown to enable greater x-ray power employs an x-ray source patterned according to a periodic pattern $A_0$. FIG. 4 illustrates an embodiment having the configuration shown in FIGS. 3A and 3B, but in which the x-ray micro-beam array 888-M is formed using such a periodic x-ray source to generate a Talbot interference pattern.

In this configuration as illustrated, the x-ray source 002 comprises an electron beam 111 bombarding an x-ray target 100 comprising a region 1001 comprising structures 700 comprising x-ray generating material embedded in a substrate 1000. The structures 700 as shown are uniform elements of size a arranged in a periodic 2-D pattern with period $p_0$. When bombarded with electrons 111, these produce x-rays 888 in a periodic pattern with period $p_0$.

The structures 700 comprising x-ray generating material may comprise a plurality of discrete finer microstructures. The x-ray generating structures may typically be arranged in a periodic pattern in one or two dimensions. X-ray sources using such structured targets are described more fully in the U.S. Patent Applications X-RAY SOURCES USING LINEAR ACCUMULATION (U.S. patent application Ser. No. 14/490,672 filed Sep. 19, 2014, now issued as U.S. Pat. No. 9,390,881), X-RAY SOURCES USING LINEAR ACCUMULATION (U.S. patent application Ser. No. 14/999,147, filed Apr. 1, 2016), and DIVERGING X-RAY SOURCES USING LINEAR ACCUMULATION (U.S. patent application Ser. No. 15/166,274 filed May 27, 2016), all of which are hereby incorporated by reference in their entirety, along with any provisional Applications to which these Patents and co-pending Patent Applications claim benefit.

Also shown in FIG. 4 are elements typical for x-ray sources: the high voltage source 010 that provides an accelerating voltage between the electron beam emitter 011 and the target 100 through electrical leads 021 and 022. The detector 290 is shown as having an array $G_D$ with a period $p_3$ equal to $p_w$, so that each micro-beam is actually uniquely detected by one detector pixel. However, as discussed above, the detector 290 is aligned such that each detector pixel corresponds to x-rays from only a single micro-beam. To facilitate this, the detector may additionally have a positioning controller 255 to align the detector pixels with the individual micro-beams.

The x-rays 888 that emerge from the arrayed source as an array of individually spatially coherent but mutually incoherent sub-sources of illumination for the beam splitting grating $G_1$ 210-2D placed at a distance L from the arrayed x-ray source $A_0$. The position of the object 240 to be illuminated by the array of micro-beams having a pitch $p_w$ is placed at a further distance D from the beam-splitting grating $G_1$ 210-2D. To ensure that each x-ray sub-source in $A_0$ contributes constructively to the image-formation process, the geometry of the arrangement should satisfy the conditions:

$$p_w = qp_0\frac{D}{L} = q\frac{p_1(D+L)}{L} \qquad \text{[Eqn. 2]}$$

where q=1 for a $\pi/2$ grating and q=0.5 for a $\pi$ grating.

This configuration is called the Talbot-Lau interferometer [see Franz Pfeiffer et al., "Phase retrieval and differential phase-contrast imaging with low-brilliance X-ray sources", Nature Physics vol. 2, pp. 258-261, 2006; and also Described in U.S. Pat. No. 7,889,838 by Christian David, Franz Pfeiffer and Timm Weitkamp, issued Feb. 15, 2011], and has been previously demonstrated using a uniform x-ray source and a masking pattern to create the x-ray source array.

It should be noted that the arrayed x-ray source may also be provided in some embodiments using a uniform x-ray material and a masked grating that allows x-rays to emerge only from specific points arranged in an array of dimension a and period $p_0$. The arrayed x-ray source disclosed above, however, may have considerable advantages over such prior art systems, as the use of discrete sources allows all generated x-rays to contribute to the image forming process. An arrayed x-ray source may also be provided by selective bombardment of an x-ray generating material using a patterned electron beam. Such sources have been described in more detail in the previously cited U.S. Patent Applications, incorporated by reference herein.

The x-ray energy spectrum of the micro-beams may be limited by the use of x-ray filters (or other means known to those in the art) to limit the x-ray bandwidth. The system of FIG. 4 is shown using such a filter 388 to filter the x-rays 888 produced by the x-ray source 002 before they encounter the beam splitting grating 210-2D. This may allow better interference contrast to be achieved. For some embodiments, having the average x-ray energy $E_0$ be between 5 keV and 100 keV, and using an x-ray filter to produce an energy bandwidth of $E_0 \pm 10\%$ or $E_0 \pm 15\%$, may be desired. The contrast between regions of greatest intensity (generally the center of the micro-beams) and the darkest intensity (generally exactly between micro-beams) is preferred to be at least 50%, but signals obtained with a contrast of more than 20%, even 10% in some cases, may be acceptable.

Figure 5:
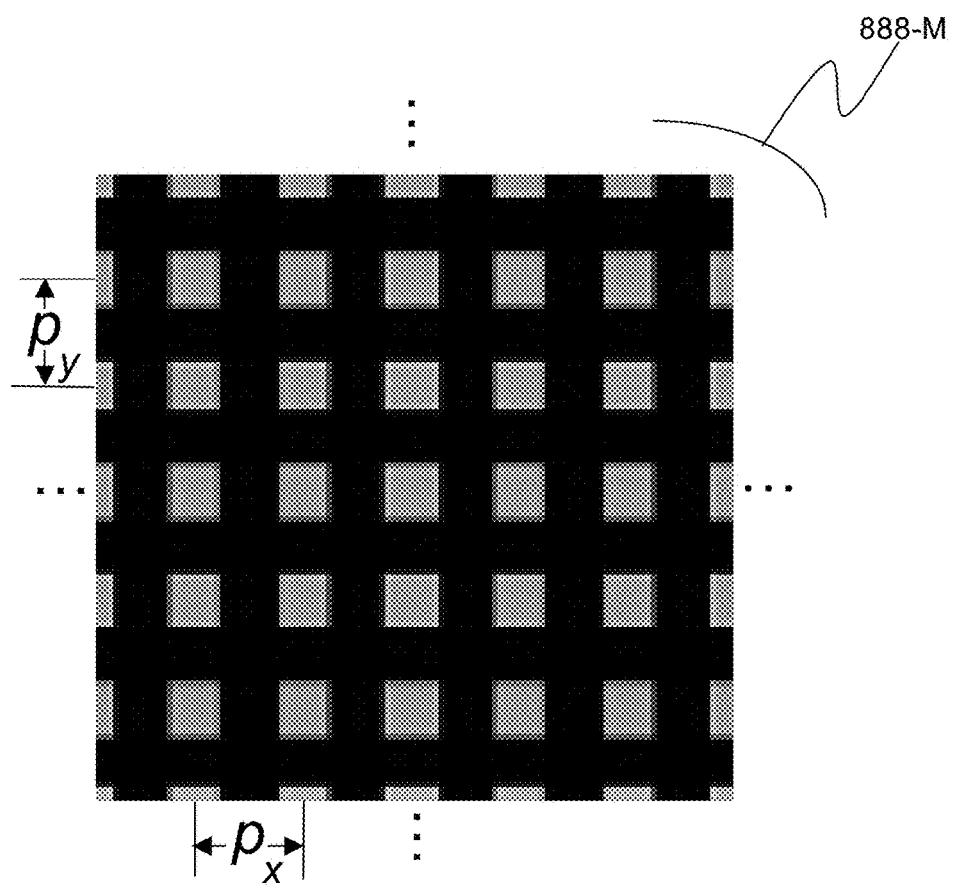
FIG. 5 illustrates a cross section of a micro-beam intensity pattern as may be formed using certain beam splitting gratings as used in some embodiments of the invention.

FIG. 5 illustrates a simulated example of a portion of a two-dimensional x-ray intensity pattern that may be created using Talbot interference fringes. If the beam-splitting grating has matching periods in x- and y-dimensions, a pattern such as that shown in FIG. 5 can be replicated at the various "depths of focus" regions of the Talbot fringes.

The beam-splitting grating may be any number of phase-shifting patterns or, in some embodiments, be formed using a pair of gratings. Typical combinations of phase shifters may use 0, $\pi/2$, or $\pi$ radian phase shifts in various regions of the grating. Combinations of 1-D patterns or 2-D patterns may also be used.

In some embodiments, it may be easier to fabricate two 1-D gratings, and mount them orthogonally to each other to create a more complex 2-D pattern. For these embodiments, the grating $G_1$ shown in FIG. 4 may be replaced with a pair of gratings $G_A$ and $G_B$ mounted together. Table I shows the various transmission values and phase shifts that may be used for such a combination of 50/50 duty cycle gratings. The values for t and $\phi$ represent the transmission and phase shifts, respectively, for two portions of each grating. A grating portion with t=0 represents an absorption transmission grating, and the phase shift of the opaque section is irrelevant.

TABLE I

Two 1-D 50/50 Crossed Grating Configurations

| Option | 1 | 2 | 3 | 4 | 5 | 6 |
|---|---|---|---|---|---|---|
| $G_A$ | t = 1, 1 | t = 1, 1 | t = 1, 1 | t = 1, 1 | t = 1, 1 | t = 0, 1 |
|  | $\phi$ = 0, $\pi/2$ | $\phi$ = 0, $\pi$ | $\phi$ = 0, $\pi$ | $\phi$ = 0, $\pi$ | $\phi$ = 0, $\pi/2$ | $\phi$ = -, 0 |
| $G_B$ | t = 1, 1 | t = 1, 1 | t = 1, 1 | t = 0, 1 | t = 0, 1 | t = 0, 1 |
|  | $\phi$ = 0, $\pi/2$ | $\phi$ = 0, $\pi$ | $\phi$ = 0, $\pi/2$ | $\phi$ = -, 0 | $\phi$ = -, 0 | $\phi$ = -, 0 |

Figure 6A:
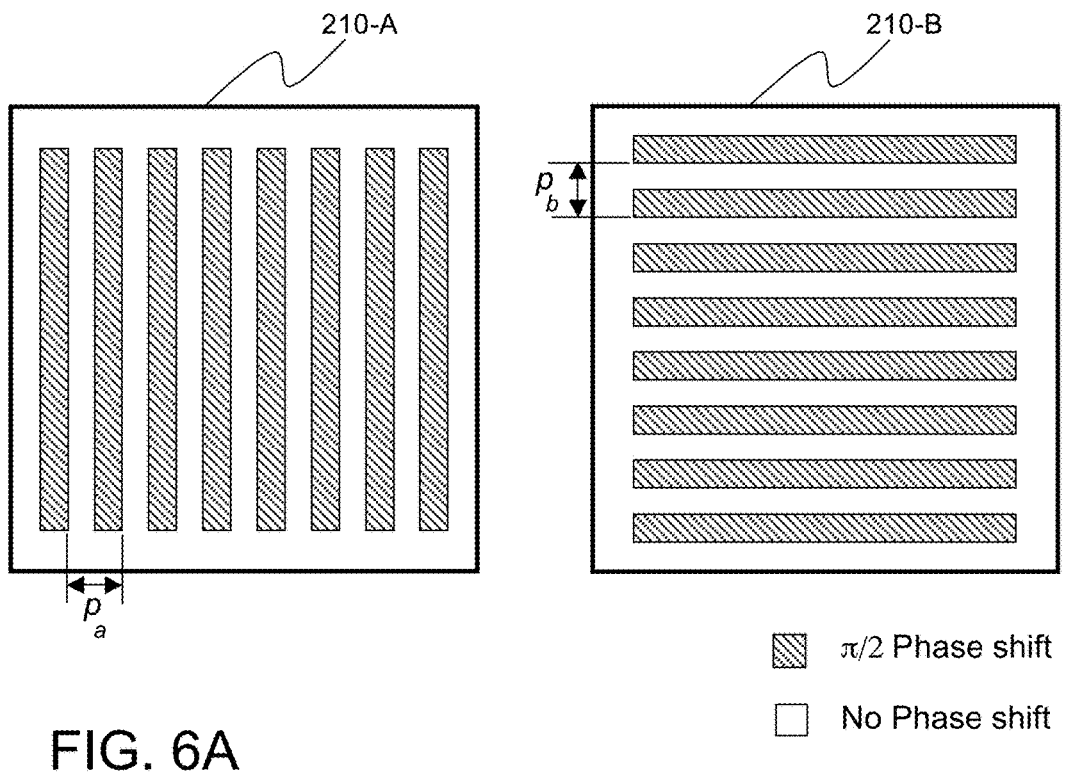
FIG. 6A illustrates a view of a pair of phase-shifting gratings as may be used in some embodiments of the invention.
Figure 6B:
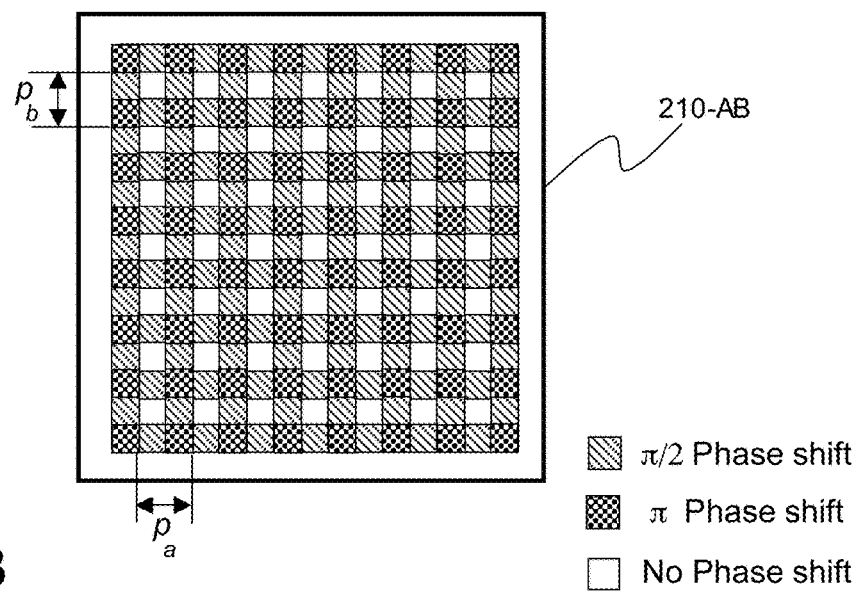
FIG. 6B illustrates the effective phase shifts that will be produced by the pair of phase-shifting gratings of FIG. 6A.

A pair of gratings for Option 1 (two crossed t/2 phase shifting gratings), in which the pitch $p_a$ for $G_A$ is the same as $p_b$ for $G_B$, is shown in FIG. 6A, and the result of the crossed gratings is shown in FIG. 6B. Such a pair of crossed gratings used as the phase shifting grating in the embodiment of FIG. 4 will form an anti-node pattern in the shape of the pattern shown in FIG. 5, with $p_x = p_y = p_a = p_b$. Other options using $\pi$ phase shifts can produce Talbot patterns having a pitch at ½ the pitch of the $\pi/2$ phase shifting gratings.

Figure 7:
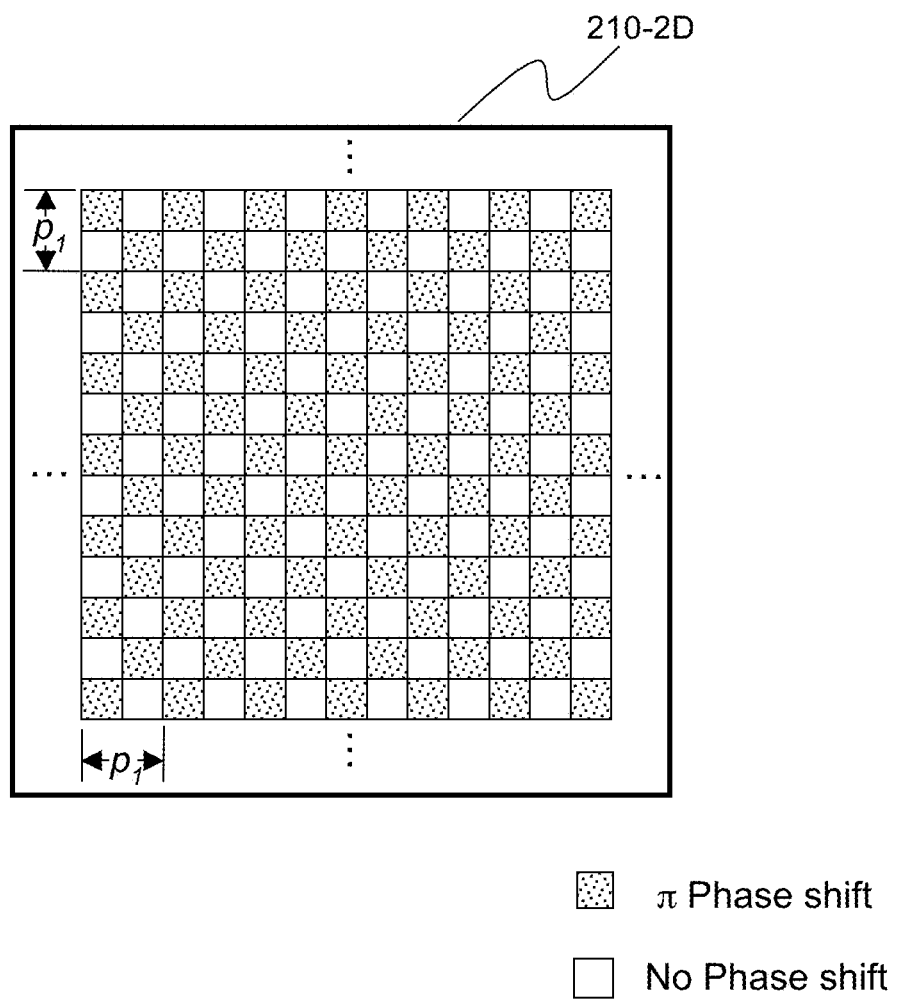
FIG. 7 illustrates a view of a t phase shifting grating as may be used in some embodiments of the invention.

Some of these configurations may also be fabricated using a single grating. For example, the crossed $\pi$ phase shifting gratings of Option 2 form a single checkerboard pattern having phase shifts of 0, $\pi$, and $2\pi=0$, which will produce the same phase shifts as the single $\pi$ phase shift checkerboard grating shown in the illustration of FIG. 7. This too should form a Talbot interference intensity pattern as was shown in FIG. 5. Likewise, other 1-D or 2-D periodic patterns of $\pi$ or $\pi/2$ phase-shifts and/or absorption gratings, as described in the previously mentioned patent applications and the other Talbot references mentioned in this Application, may also be used.

To ensure that the object 240 to be examined is illuminated by a periodic pattern of x-ray micro-beams 888-M, the distance D between the grating and the object should correspond to one of the fractional Talbot distances, i.e.

$$D = n\frac{p_1^2}{8\lambda} \qquad \text{[Eqn. 3]}$$

where n is a non-zero integer. The suitable value of n may be different if the grating is an absorption grating, a $\pi$ phase-shifting grating, or a $\pi/2$ phase-shifting grating.

For more general situations, in which diverging/magnifying fringes, may be used, this distance may be generalized to $$D = \frac{(n/8)p_1^2 L}{(\lambda L - (n/8)p_1^2)} \qquad \text{[Eqn. 4]}$$

Another equation often used in Talbot-Lau systems relates the pitch $p_1$ of the Talbot grating $G_1$ to the size a of the x-ray generating elements in the arrayed source:

$$p_1 \geq L\frac{\lambda}{a} \qquad \text{[Eqn. 5]}$$

Most embodiments of the invention employ a interferometric system in which the conditions presented in Eqns. 2-5 are met.

It should be noted that these embodiments as illustrated are not to scale, as the divergence, collimation, or convergence of the Talbot interference pattern will depend on factors such as the x-ray energy, on how well collimated the x-ray beam is and how far the object is placed from the source.

3. Detector Considerations.

As disclosed here, the detector pitch will be matched to the pitch of the multiple Talbot fringes so that each pixel is positioned to only detect x-rays emerging from the interaction of the object with a single micro-beam, and the crosstalk between pixels due to neighboring micro-beams is minimized. Then, the data collection and final reconstruction of the "map" of the properties of the object may proceed, knowing that the distinct signals from each pixel need not be further deconvolved.

If there is cross-talk between micro-beams and pixels (e.g. due to scattering or fluorescence), additional image analysis may be able to remove some of the cross-talk if it can be properly calibrated. Energy resolving array detectors may also be used to separate signals from transmitted x-rays, refracted x-rays, scattered x-rays, and fluorescence x-rays.

This matching is most straightforwardly achieved if the detector pitch is a 1:1 match to the pitch of the micro-beams, i.e. each beam has a corresponding single pixel in the detector, and the detector is placed in proximity to the object and the micro-beams.

3.1 Finer Detector Pitch.

In some embodiments, detector pitches that are integer fractions of the pitch of the micro-beams (e.g. a 3× reduction in pitch, which would indicate 9 pixels are present to detect the x-rays corresponding to each micro-beam) may also be used. This may offer some advantages if the x-rays being detected have some spatial structure, for example if the desired x-ray signal is related to small-angle scattering from the object. Then, certain pixels of the detector can be aligned to detect only the scattered x-rays, while the non-scattered beam may be collected by a different pixel, or simply blocked by a blocked pixel.

3.2. Larger Detector Pitch.

In other embodiments, a detector pixel that is larger than the pitch of the micro-beam may be used. The detector may therefore be less expensive, and yet still produce a "high resolution" signal (since the spatial resolution is determined by the interaction volume of the Talbot fringe and the object, not the detector pixel size).

One disadvantage of this technique is that only 1 out of 4 micro-beams is used for detection, and the other micro-beams are blocked. With a larger pixel, greater detection efficiency may be achieved for the micro-beams that are detected.

Figure 8:
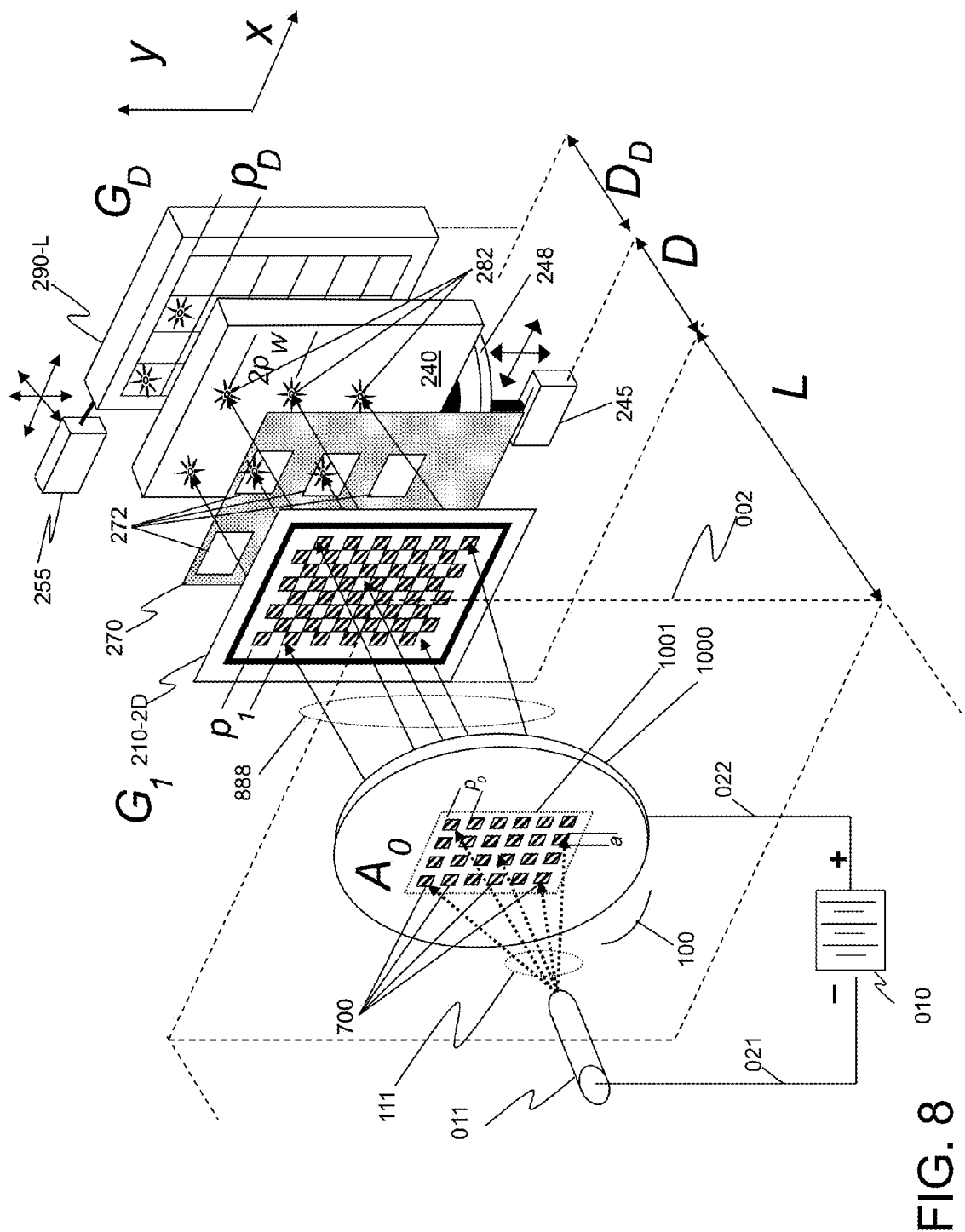
FIG. 8 illustrates a schematic view of a microscope according to an embodiment of the invention having a mask placed in front of the object under examination.

FIGS. 8-15 illustrate the use of larger pixels in some embodiments of the invention. FIG. 8 illustrates a schematic of an embodiment of a system similar to that of FIG. 4, but in which a mask 270 with a number of apertures 272 has been placed in front of the object 240 to block a certain number of micro-beams. As illustrated, 3 out of every 4 micro-beams are blocked, with only 1 beam out of each 4 beams proceeding to illuminate the object and then be detected by the detector. This means that if the pitch of the x-ray beams at the mask is $p_W$, the pitch of the beams illuminating the object is $2p_W$. The detector pitch $p_D$ may therefore be set to be equal to $2p_W$ as well, larger than was used for the configuration in FIG. 4. As illustrated, 3 of 4 beams are blocked, but any number of beams may be blocked according to any number of predetermined patterns for various applications.

Figure 9A:
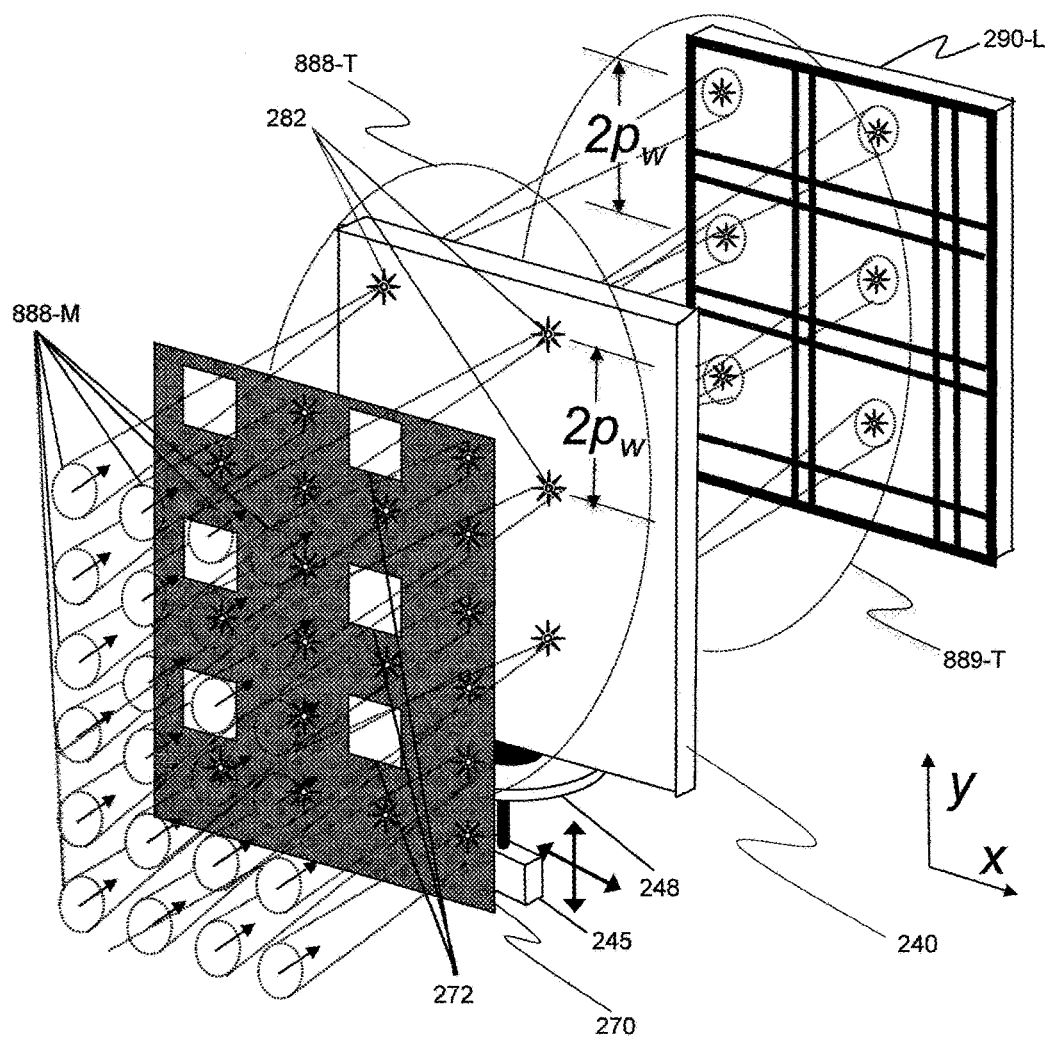
FIG. 9A illustrates a schematic view of the micro-beams, object, and detector of the embodiment of FIG. 8.
Figure 9B:
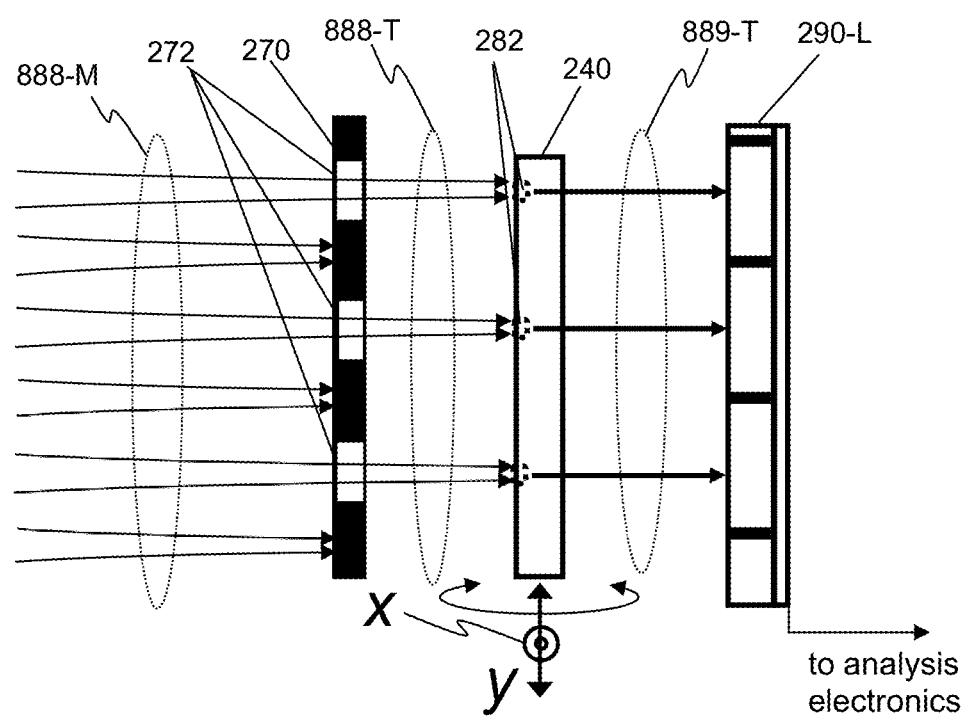
FIG. 9B illustrates a schematic cross-section view of the micro-beams, object, and detector of the embodiment of FIG. 8.

FIGS. 9A and 9B illustrate such an embodiment in more detail, presenting illustrations similar to those of FIGS. 3A and 3B. As can be seen by the comparison with FIGS. 3A and 3B, because only a certain number of micro-beams are used, the pitch of beams at the detector is substantially larger, and a less expensive detector 290-L with a larger pixel size may be used.

As illustrated up to this point, the x-ray detector is presented as a direct array detector, generating an electrical signal in response to the absorption of x-rays. Some embodiments may use direct flat panel detectors (FPDs) such as the Safire FPD of Shimadzu Corp. of Kyoto, Japan. Some embodiments may use complementary metal-oxide semiconductor (CMOS) imagers. Some embodiments may use energy resolving array detectors.

In other embodiments, the detector may use scintillators that emit visible or ultraviolet light when exposed to x-rays. The active x-ray detection region (the detector sensors) may be defined, for example, by providing a scintillator such as cesium iodide doped with thallium (CsI: Tl) or by providing a detector with a uniform coating of scintillator with a masking layer of high Z material, for example, gold (Au), on top.

Figure 10:
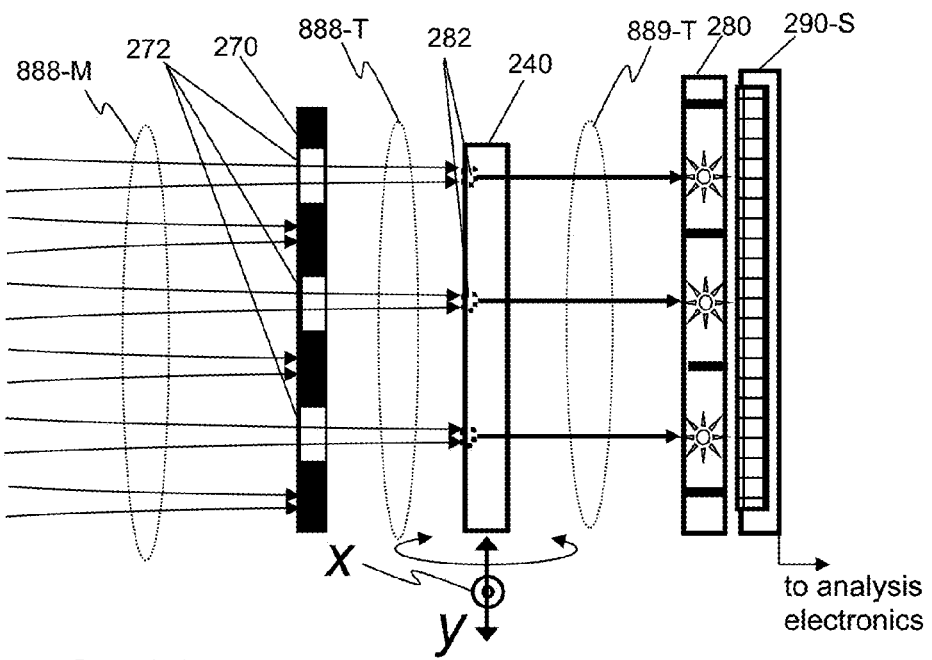
FIG. 10 illustrates a schematic cross-section view of the micro-beams, object, and detector of an embodiment comprising a scintillator detector.

FIG. 10 illustrates a variation of the embodiment of FIG. 9B, but using a detector 290-S in combination with a fluorescent screen or scintillator 280. The scintillator 280 comprises a material that emits visible and/or UV photons when x-rays are absorbed, and the detector 290-S detects those visible and/or UV photons. Typical scintillator materials comprise a layer of thallium doped CsI, Eu doped Lutetium Oxide ($Lu_2O_3$: Eu), yttrium aluminum garnet (YAG), or gadolinium sulfoxylate (GOS).

The scintillator efficiency depends upon the fraction of x-rays absorbed by the scintillator and the amount of light produced by the scintillator. For high resolution, the lateral spread of light within the scintillator should be minimized and this often necessitates use of a thin scintillator which may limit x-ray absorption and hence detection efficiency.

In conventional imaging systems, high resolution images with a scintillator-type detector in close proximity to the object can be obtained, but the overall thickness of the scintillator and electronic elements must be thin enough so that each detector pixel is collecting only x-rays corresponding to that pixel. This may also dictate the use of a thinner scintillator, reducing the ultimate sensitivity.

However, in the embodiments disclosed in this Application, the spatial resolution is defined by the dimensions of the micro-beams 888-M instead of the detector pixel size. This allows a larger pixel and thereby a thicker scintillator material with higher efficiency to be used, since every photon generated from the larger pixel will be known to have originated from a predetermined micro-beam.

Figure 11:
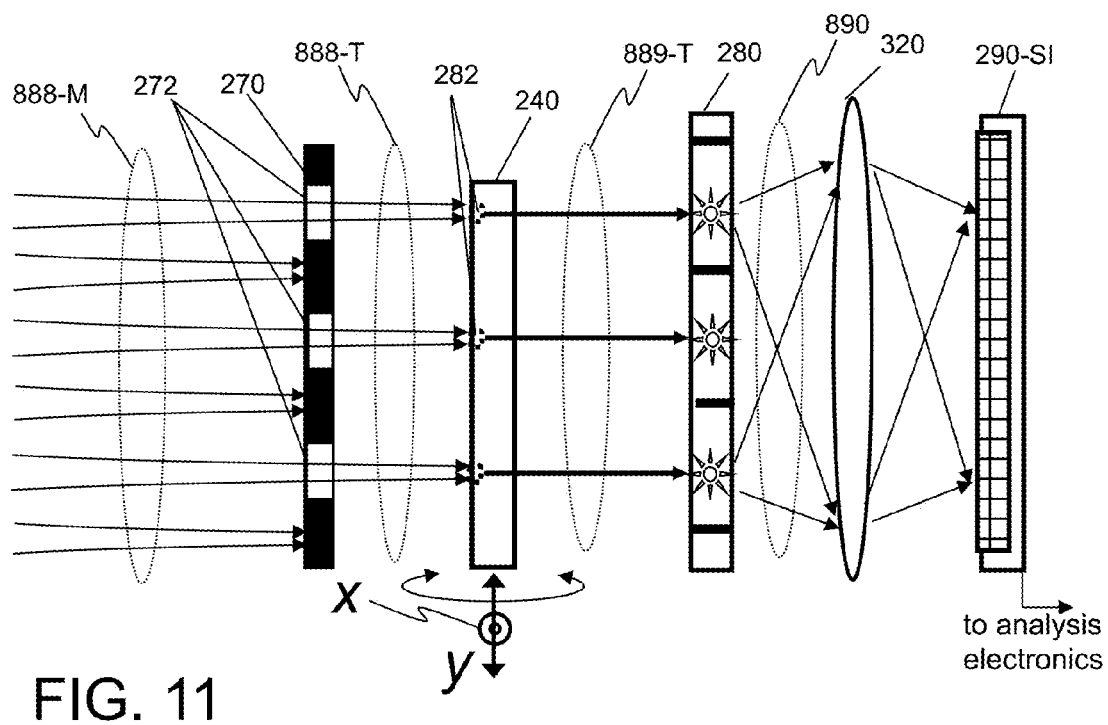
FIG. 11 illustrates a schematic cross-section view of the micro-beams, object, and detector of an embodiment comprising a scintillator and a scintillator imaging system.

FIG. 11 illustrates an additional variation on a system using a scintillator, in which the visible/UV light 890 from the scintillator 280 is collected by a visible/UV optical system 320 and imaged onto a detector 290-SI. The visible/UV optical system may comprise optics with additionally magnify the image of the scintillator. When using relay optics and a magnified image, the electronic detector need not comprise a high resolution sensor itself, and less expensive commercial CCD detectors or complementary metal-oxide-semiconductor (CMOS) sensor arrays with, for example, 1024×1024 pixels, each 24 µm×24 µm square, may be used.

Thicker scintillators may also be used in some embodiments having relay optics, increasing sensitivity. However, when relay optics are used, detection is limited to the field of view collected by the x-ray optics, which may in some cases be only on the order of hundreds of microns. Collecting data on larger areas can only be accomplished if images are "stitched" together from several exposures.

Figure 12:
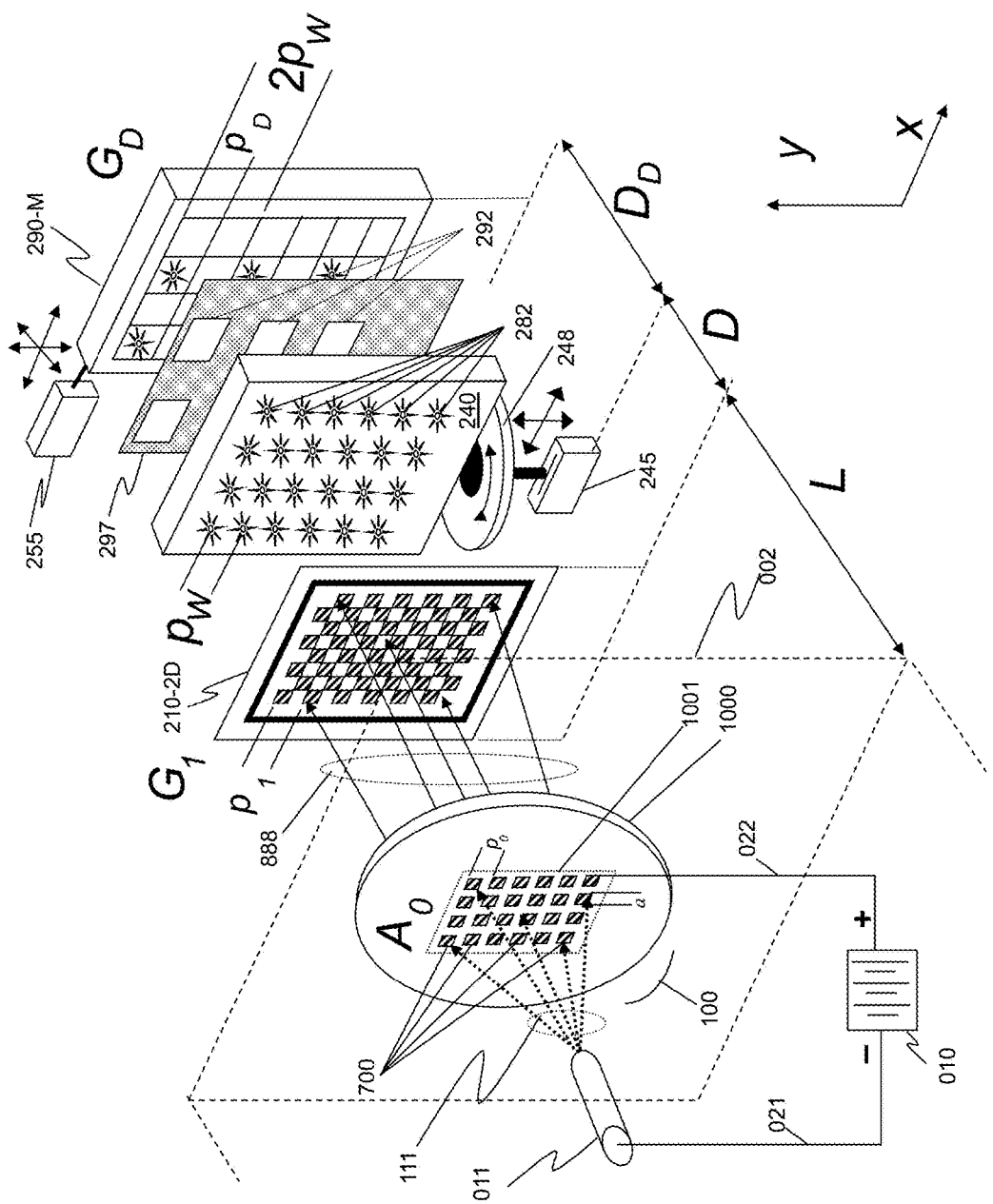
FIG. 12 illustrates a schematic view of a microscope according to an embodiment of the invention having a mask placed between the object under examination and the detector.
Figure 13A:
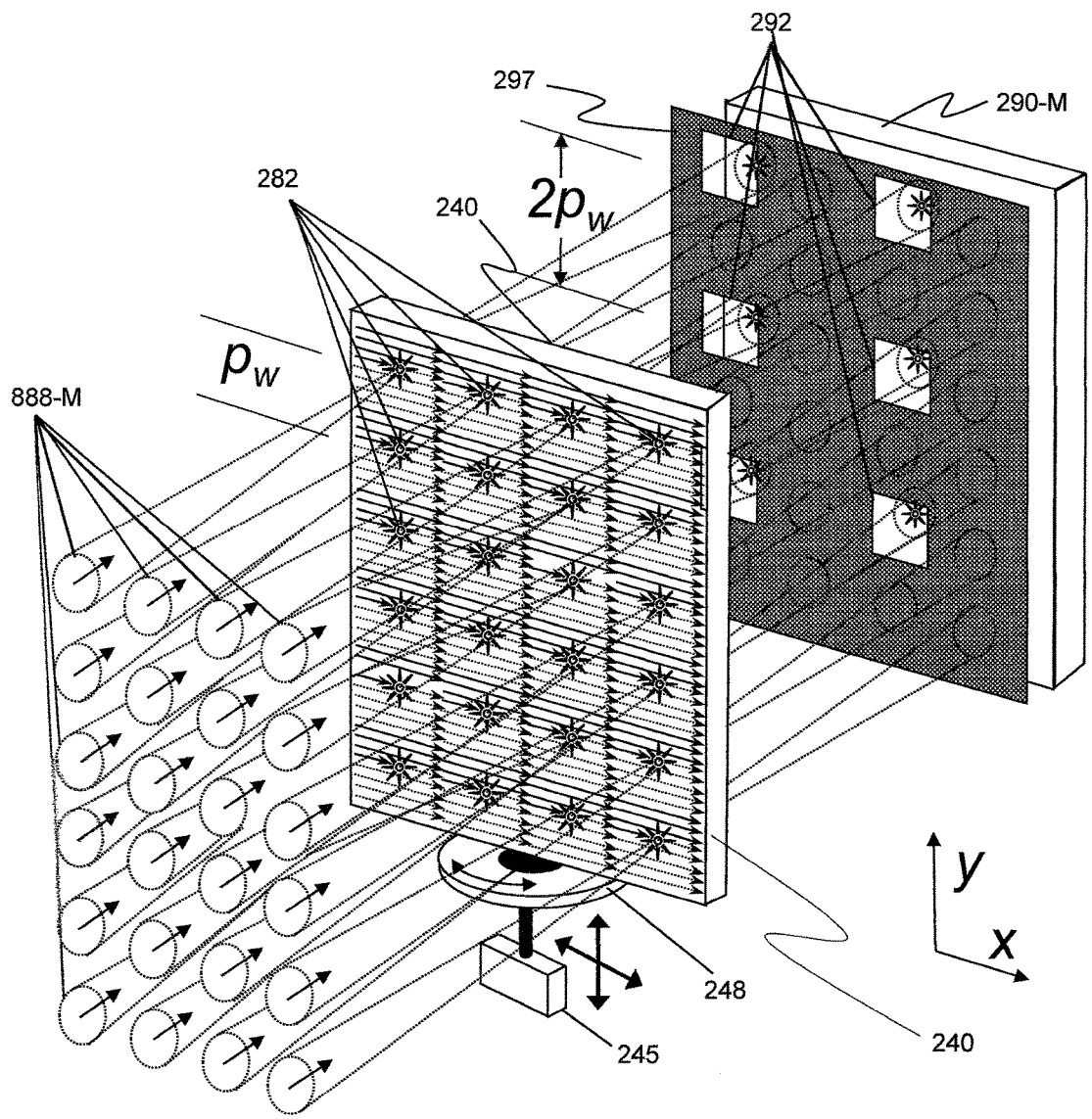
FIG. 13A illustrates a schematic view of the micro-beams, object, and detector of the embodiment of FIG. 12.
Figure 13B:
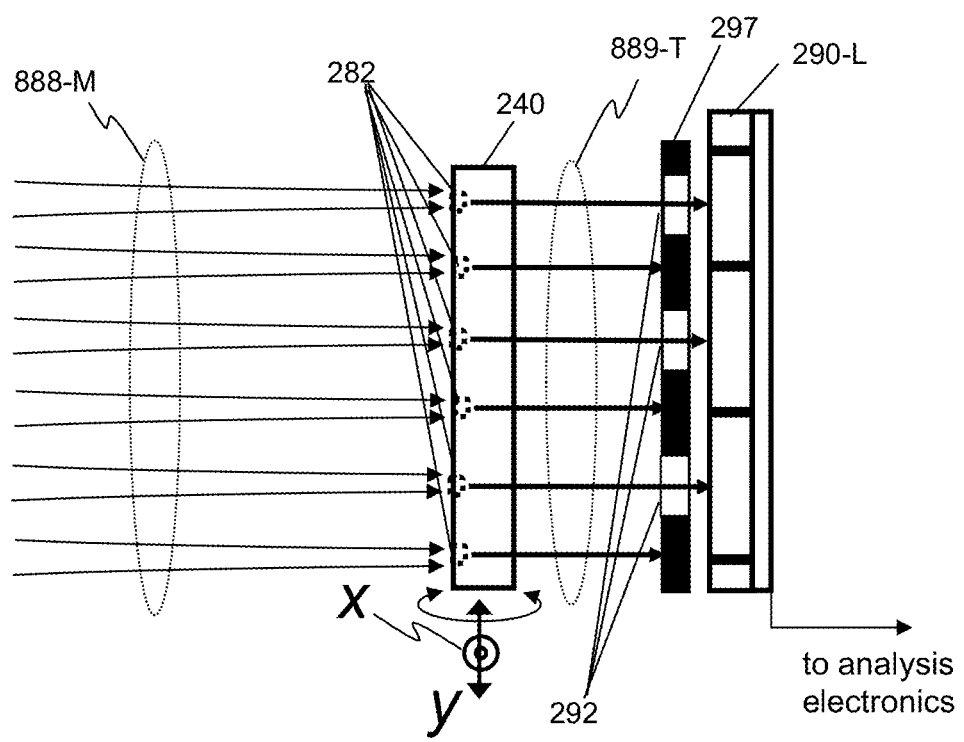
FIG. 13B illustrates a schematic cross-section view of the micro-beams, object, and detector of the embodiment of FIG. 12.

FIGS. 12, 13A and 13B represent an additional embodiment in which a masking structure 297 with apertures 292 is placed between the object 240 and the detector 290-M. For this embodiment, all available micro-beams 888-M illuminate the object 240, but a masking layer 297 made of, for example, gold (Au), prevents 3 out of every 4 beams from entering the detector 290-M. This also allows detector 290-M to have a larger pixel, again reducing cost for direct detectors and, for embodiments using scintillators, increasing potential detector efficiency.

Figure 14:
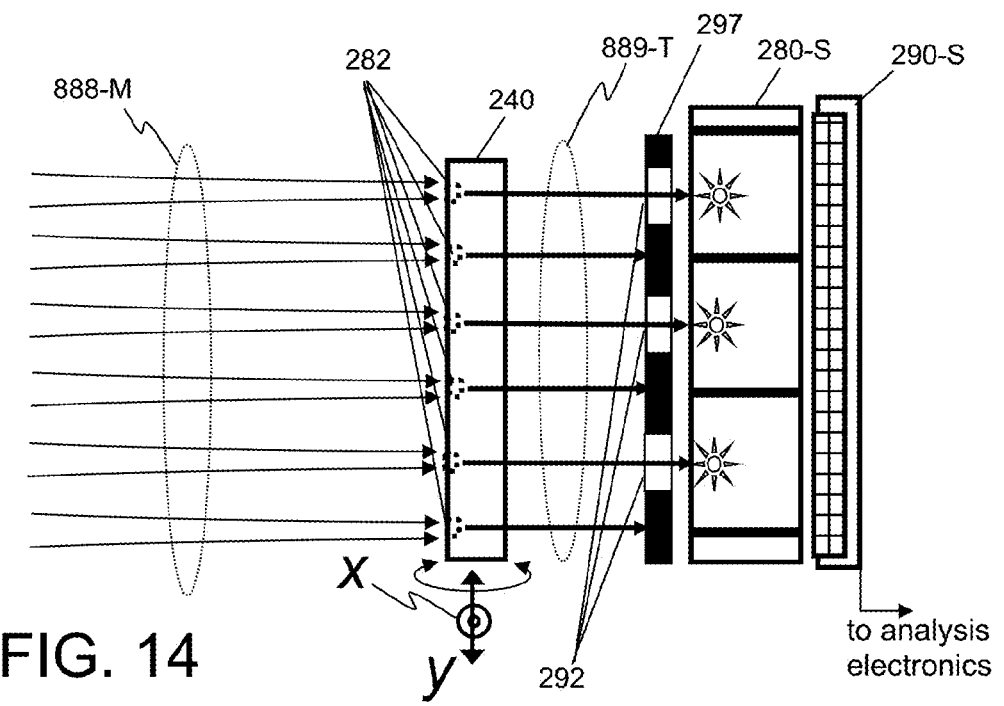
FIG. 14 illustrates a schematic cross-section view of the micro-beams, object, and detector of an embodiment comprising a mask at the detector and a scintillator.

FIG. 14 illustrates an additional variation of the embodiment of FIGS. 10, 11A and 11B, but with the detection of x-rays achieved using a thicker scintillator 280-S and a visible/UV light detector 290-S.

Figure 15:
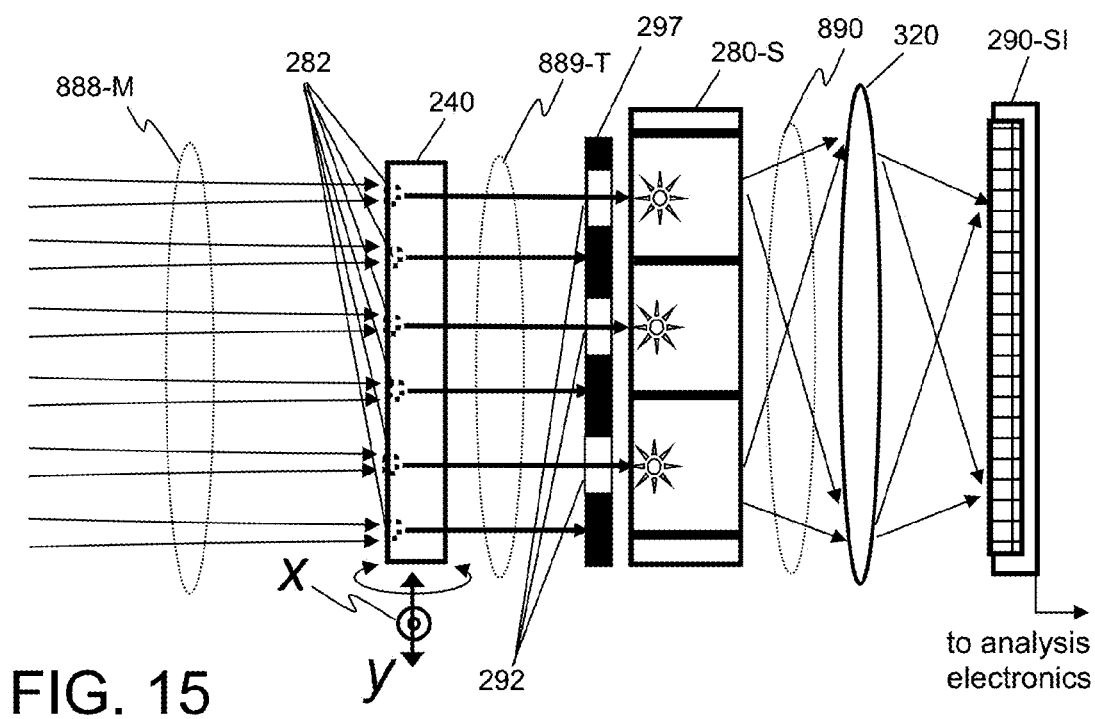
FIG. 15 illustrates a schematic cross-section view of the micro-beams, object, and detector of an embodiment comprising a mask at the detector and a scintillator and a scintillator imaging system.

FIG. 15 illustrates an additional variation on a system using a scintillator, in which the visible/UV light 890 from the scintillator 280 is collected by a visible/UV optical system 320 and imaged onto a detector 290-SI.

Commercial flat panel digital x-ray sensors in which a layer of scintillator material is placed in close proximity to (or even coated onto) an array of conventional optical image sensors are manufactured by, for example, Varian Inc. of Palo Alto, Calif. and General Electric, Inc. of Billerica, Mass. Other configurations of image sensors may be known to those skilled in the art.

Although the scintillators as illustrated in FIGS. 10, 11, 14, and 15 are shown as comprising uniform layers of scintillator, embodiments using patterned scintillator material, in which scintillator material is placed only over a portion of the pixel, may also be used. The selective placement of scintillator material over portions of the detector may be used as an alternative to the use of a masking layer to select certain micro-beams for detection.

Detectors with additional structure within each pixel may also be employed as well. For example, if the typical detector pixel is 2.5 microns by 2.5 microns (an area of 6.25 micron), but the micro-beam diameter is only 1 micron, a detector pixel with a central "spot" of scintillator material slightly larger than 1 micron and positioned to correspond to the position of the micro-beam may be created. With this configuration, all the x-rays from the micro-beam should be detected, while reducing the detection of scattered or diffracted x-rays that would otherwise cause spurious signals if the full area of the detector pixel were to be used.

Likewise, pixels in which detector structures (such as scintillator material) are only positioned on the outer portion of the pixel, for example, to only detect x-rays scattered at small angles while not detecting the directly transmitted beam, may also be used for some embodiments.

Similarly, although the mask 297 in FIGS. 13 and 14 is shown as displaced from the scintillator 280, some embodiments may have the mask 297 directly deposited onto the scintillator 280. Other embodiments for patterned scintillators may be known to those skilled in the art.

3.3. Detector Variations.

The descriptions above disclose embodiments in which certain portions of the detector are not used for detecting x-rays by using a masking layer to block some number of micro-beams. Similar masking effects may be achieved for some configurations by using an array detector in which certain pixels are simply made inactive, either by removing power from the inactive pixels, so they do not produce a signal, or by using analysis software that ignores or eliminates any signals being generated by the "inactive" pixels. These "inactive" pixels serve the same function as the space between pixels 291-A, as was illustrated in FIG. 3C.

These inactive regions may also be regions transparent to x-rays, allowing the use in some embodiments of multiple detectors. In such embodiments, each detector is positioned to detect only a selected number of the x-ray beams. This may be done by using a detector with pixels designed to detect only a predetermined number of the beams, while allowing other beams to pass through the detector.

Figure 16:
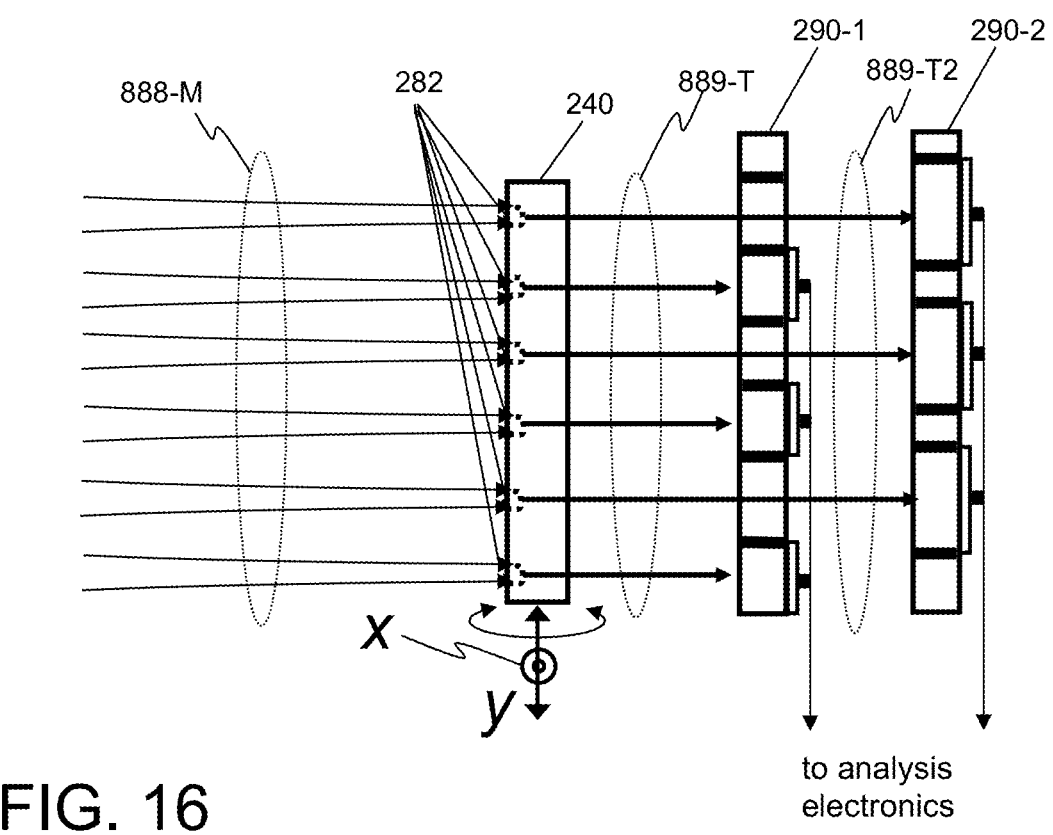
FIG. 16 illustrates a schematic cross-section view of the micro-beams, object, and detectors for an embodiment comprising multiple detectors.

Such a configuration is illustrated in FIG. 16. The first detector 290-1 is an array detector with a pixel sized to detect all the transmitted x-rays corresponding to a single micro-beam, transmissive regions between the pixels. Micro-beams incident upon these transmissive regions then pass through the detector 290-1, and fall onto a second detector 290-2 with pixels aligned to detect these alternative x-ray micro-beams.

In some embodiments, the first detector 290-1 may be transmissive over the entire region to high energy x-rays and the first detector 290-1 is used to detect the lower energy x-rays while the second detector 290-2 is used to detect higher energy x-rays. Such a configuration may include two, three, or more detectors, depending on how many pixels are activated in the first detector and how many micro-beams are allowed to pass through the first detector to be detected or pass through the second detector. The advantage of this approach over the masking approach is that each x-ray micro-beam is eventually detected and can contribute to the final collected data set.

4.0 Methods of Microscopic Data Gathering.

Figure 17A:
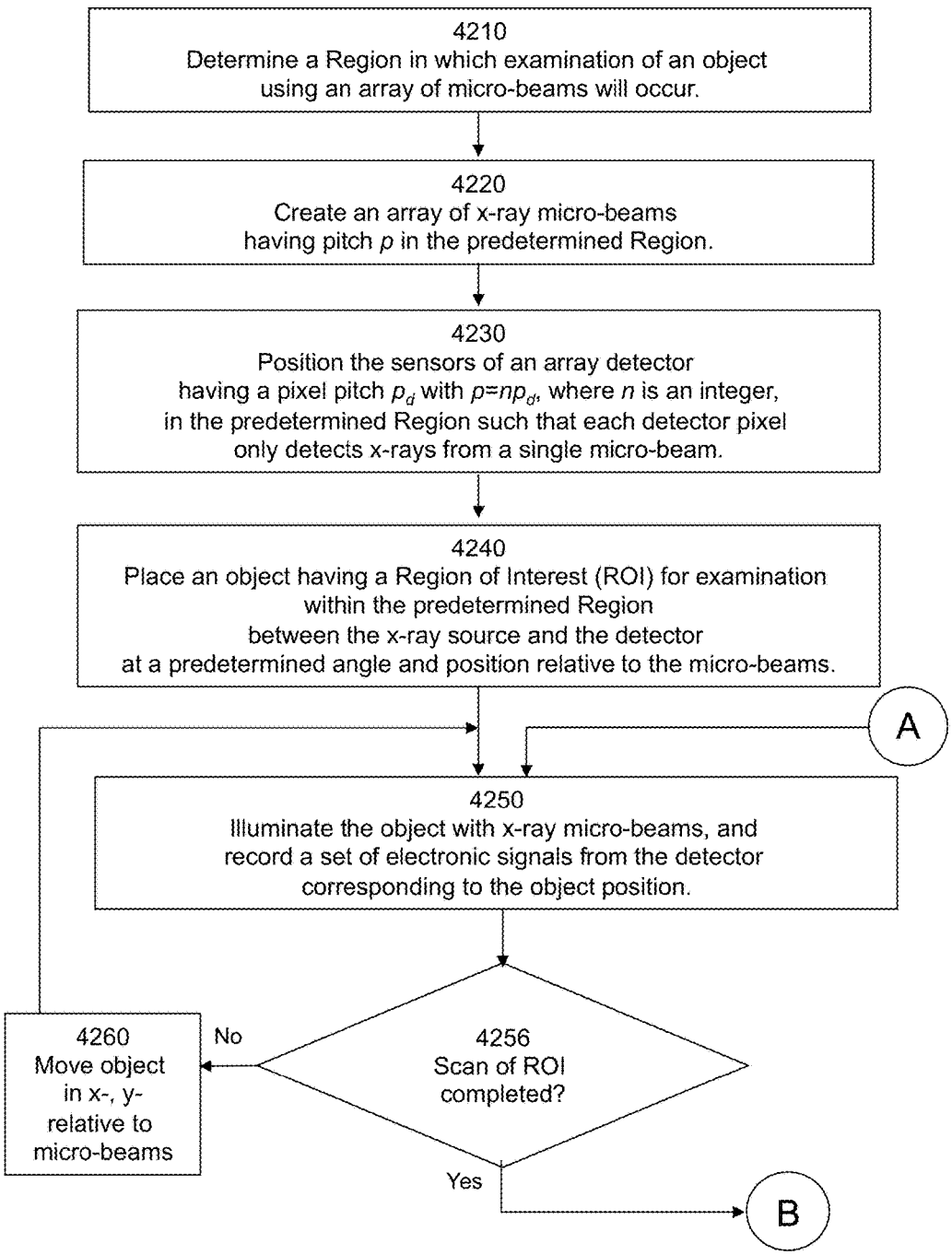
FIG. 17A presents a portion of the steps of a method for collecting microscopy data according to an embodiment of the invention.
Figure 17B:
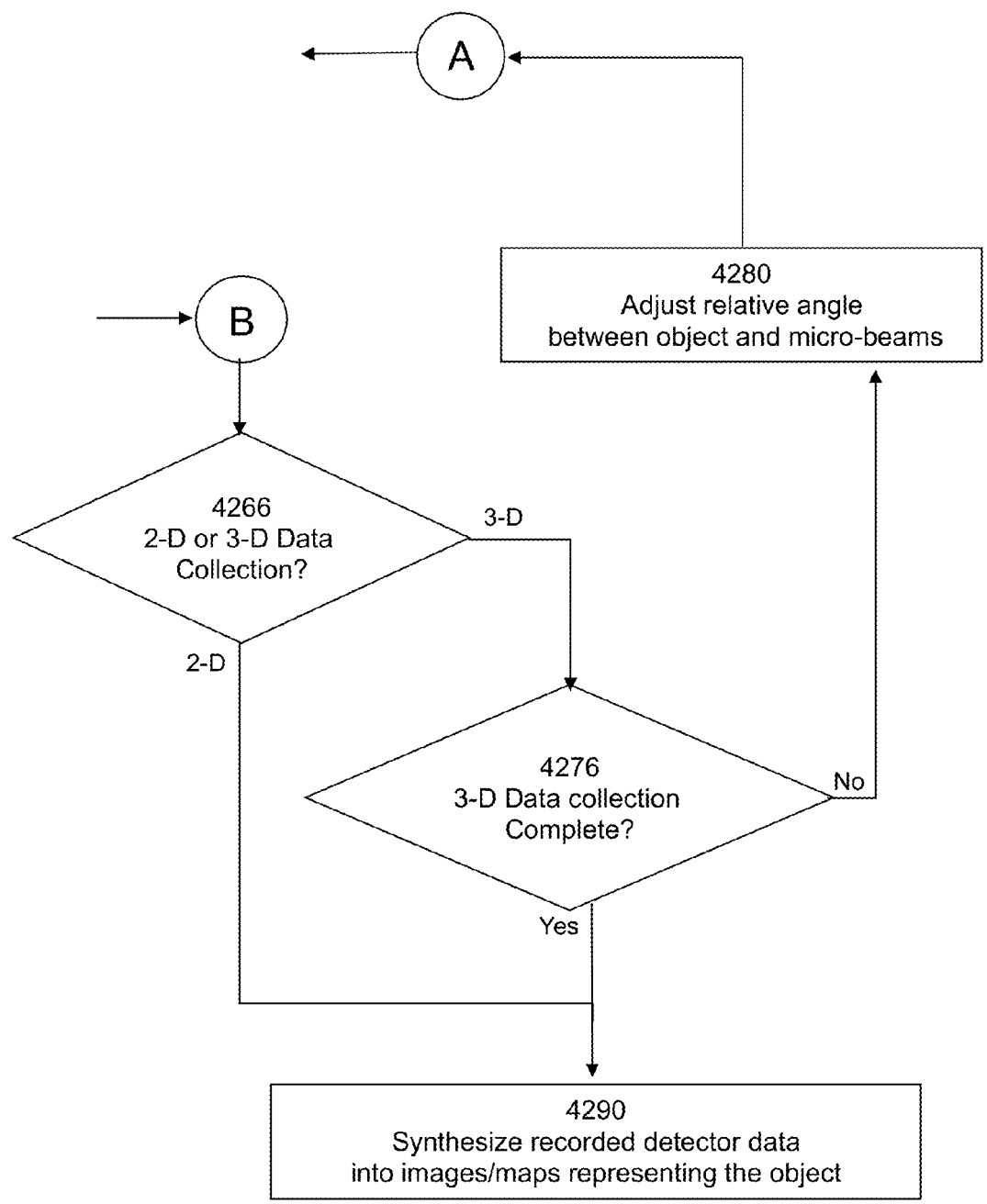
FIG. 17B presents the continuation of the steps of the method of FIG. 17A for collecting microscopy data according to an embodiment of the invention.

The process steps to form an image using micro-beams according to an embodiment are represented in FIGS. 17A and 17B, and are described below.

In the first step 4210, a region of space in which the object will be examined by an array of micro-beams is determined. This region may be a region bounded by the "depth of focus" discussed above for the micro-beams, or may be defined as a region related to a fraction of the Talbot distance $D_T$ for a given Talbot pattern, or by any criteria suitable to the measurements desired.

In step 4220, an array of micro-beams having a pitch p is formed in the predetermined region. Such micro-beams may be formed by any of the disclosed methods, including by using an x-ray imaging system or by using Talbot interference phenomena. In some embodiments, such as when the interference field is formed by a Talbot interference pattern, this region may be defined as a region with a length related to a fractional Talbot distance, e.g. ⅛ $D_T$ or 1/16 $D_T$.

The micro-beams within this region may have a lateral pattern in the form of an array of circular beams or beams with a square or rectangular profile. The array of micro-beams will generally be propagating in a single direction (generally designated the "z" direction), with a pitch p between micro-beams in the directions orthogonal to the propagation direction (the "x" and "y" directions) being 20-50 micrometers or less.

In some embodiments, this step may also be used to insert an additional mask that removes some of the micro-beams, as discussed above.

Once the micro-beam region has been established, the next step 4230 is the placement of a detector having a pixel pitch $p_d$ equal to a non-zero integer multiple of the micro-beam pitch p. The detector may be any of the detectors as described above. This sensor portion of the detector is placed in the region selected in the previous step. There is some flexibility in the exact positioning of the detector, as long as each pixel of the detector generates a signal corresponding only to a single micro-beam (without cross-talk between the micro-beams or detector pixels). Generally, a detector will be chosen where every micro-beam has a corresponding pixel or set of pixels; however, in some embodiments, the detector may only detect a subset of the corresponding micro-beams.

In the next step 4240, a region of interest (ROI) of an object to be examined is placed in the selected region comprising micro-beams as well, between the x-ray source and the front of the detector. This will generally be in proximity to the detector, so that the object and detector are both within a "depth-of-focus" region of the micro-beam. Typically, the x-ray beam will either be blocked or turned off while the object is positioned and aligned, and the x-rays turned on after the object has been placed.

In the next step 4250, the x-rays transmitted by each micro-beam are detected by the corresponding pixels on the detector, and the corresponding electronic signals are recorded. These signals may represent x-ray intensity in counting detectors and may also include energy in energy-resolving detectors.

In the next step 4256, a decision on how to proceed is made. If only a single set of datapoints are desired, no more data need be collected, and the method proceeds to the step indicated by "B" in FIGS. 17A and 17B. If, on the other hand, additional data need to be collected to build up a 1-D or 2-D "map" of the properties of the object, the decision tree delivers a request for data from additional positions.

In the next step 4260, the relative position of the object and the micro-beams is changed by a predetermined distance in x- and/or y-dimensions, and the method reverts to step 4250, in which data is now collected for the new position. The system will loop through this decision tree of steps 4250, 4256, and 4260 until data have been collected for the entire 1-D or 2-D region designated for examination, at which point the method proceeds to the step indicated by "B" in FIGS. 17A and 17B.

Once one set of 2-D scanning data has been collected, the system will determine in steps 4266 and 4276 whether only a 2-D "map" is to be constructed, or if additional information is needed to generate a 3-D representation of the object, using algorithms related to either laminography or tomography.

If no information beyond what has been acquired is needed, the method proceeds to the final analysis step 4290. If data for a 1D or 2D map was taken in the previous steps, the accumulated data is then used with various image "stitching" techniques that are generally well known in the art to synthesize a 1-D or 2-D intensity "map" representing the x-ray transmission/absorption of the ROI of the object.

If, on the other hand, 3-D information is desired, in the next step 4276, a decision on how to proceed is made. If additional data is still required to be collected to build up a 3-D dataset of the properties of the object, the decision tree delivers a request for data from additional angles.

The method then proceeds to a step 4280 in which the object is rotated by a predetermined angular increment around an axis at a predetermined angle relative to the z axis, and then the method proceeds to the step indicated by "A" in FIGS. 17A and 17B, passing control back to the loop of steps 4250, 4256, and 4260 to collect a set of data from the x-ray detector at this alternative rotation position.

The system will loop through these steps 4250, 4256, 4260 and also 4266, 4276, and 4280 to collect x-ray information at a preprogrammed sequence of positions and rotations until a complete set of data is collected. At this point, after all data collection is complete, the system will then proceed to the final analysis step 4290 to take the accumulated data and, in this case, use various image 3-D analysis techniques that are generally well known in the art, to synthesize a 3-D representation of the x-ray transmission/absorption of the object ROI.

Variations on the method described above may also be put into practice. For example, instead of first executing a loop of data collection in x- and y-dimensions at a fixed rotation position, and then changing the rotation setting to collect additional data, embodiments in which the object is rotated while the x- and y-position settings remain fixed may also be executed. Rotation of the object around the z-axis may also provide additional information that can be used in image tomosynthesis.

5. Limitations and Extensions.

With this Application, several embodiments of the invention, including the best mode contemplated by the inventors, have been disclosed. It will be recognized that, while specific embodiments may be presented, elements discussed in detail only for some embodiments may also be applied to others. Also, details and various elements described as being in the prior art may also be applied to various embodiments of the invention.

While specific materials, designs, configurations and fabrication steps have been set forth to describe this invention and the preferred embodiments, such descriptions are not intended to be limiting. Modifications and changes may be apparent to those skilled in the art, and it is intended that this invention be limited only by the scope of the appended claims.

We claim:

1. A method of examining an object with x-rays, comprising:
    creating a periodic array of x-ray micro-beams propagating from a common x-ray source, with each x-ray micro-beam at the object having an axis along which the x-ray micro-beam propagates, and having a contrast between the x-ray intensity along the axis and the x-ray intensity at a distance equal to ½ of the period of said periodic array of x-ray micro-beams measured perpendicularly from said axis of greater than 10%;
    positioning an x-ray pixel array detector system comprising a plurality of pixels so that each pixel detects x-rays corresponding to no more than one x-ray micro-beam;
    illuminating a portion of said object with said periodic array of x-ray micro-beams; and
    recording signals produced by said x-ray pixel array detector system.

2. The method of claim 1, wherein the periodic array of x-ray micro-beams is created through Talbot interference phenomena that form a Talbot interference pattern; and said x-ray micro-beams correspond to an array of constructive interference portions of the Talbot interference pattern.

3. The method of claim 2, additionally comprising:
    positioning an absorbing masking component having periodic transmissive portions that transmit only a predetermined subset of the x-ray micro-beams; wherein the period of said transmissive portions in both lateral directions is equal to the period of the Talbot interference pattern multiplied by a positive integer N; and
    aligning said absorbing masking component so that said transmissive portions are centered with every Nth x-ray micro-beam.

4. The method of claim 1, additionally comprising positioning placing an absorbing masking component having transmissive portions to transmit only a predetermined subset of the x-ray micro-beams.

5. The method of claim 4, wherein the lateral dimensions of said transmissive portions are less than ¾ of the period of the periodic array of the x-ray micro-beams.

6. The method of claim 1, additionally comprising positioning the x-ray pixel array detector system so that two or more pixels detect x-rays corresponding to the same x-ray micro-beam.

7. The method of claim 1, wherein the signals correspond to the transmission of said x-ray micro-beams through the object.

8. The method of claim 1, wherein the signals correspond to an interaction phenomenon of said x-ray micro-beams with the object, said interaction phenomenon selected from the group consisting of: absorption, refraction, x-ray fluorescence, and small angle scattering.

9. The method of claim 1, wherein the x-ray pixel array detector system comprises a first x-ray detector having periodic x-ray active areas positioned to detect x-rays and to produce signals corresponding to said x-rays, the periodic x-ray active areas separated by x-ray inactive areas that do not produce signals, with the period of said periodic x-ray active areas configured to detect only a predetermined subset of the x-ray micro-beams.

10. The method of claim 9, wherein the x-ray inactive areas transmit x-rays, and the x-ray pixel array detector system additionally comprises a second x-ray detector positioned to detect the x-rays transmitted through the first x-ray detector.

11. The method of claim 1, wherein the period of the periodic array of x-ray micro-beams at the object is less than 50 micrometers.

12. The method of claim 1, wherein the length of each x-ray micro-beam along said axis at the object is greater than 1 millimeter.

13. The method of claim 1, additionally comprising:
laterally displacing relative positions of the object and the periodic array of x-ray micro-beams in at least one direction perpendicular to the axis of one of the x-ray micro-beams by one or more times;
recording signals produced by said x-ray pixel array detector system after each lateral displacement has occurred; and
generating a two-dimensional image using said recorded signals.

14. The method of claim 13, wherein laterally displacing the relative positions of the object and the periodic array of x-ray micro-beams is carried out by laterally displacing the object.

15. The method of claim 1, additionally comprising:
changing a relative angular orientation of the object and the periodic array of x-ray micro-beams one or more times by an angle of 0.5 degrees or more;
recording signals produced by said x-ray pixel array detector system after each change of the relative angular orientation has occurred; and
generating a three-dimensional image using said recorded signals.

16. The method of claim 15, wherein changing the relative angular orientation of the object and the periodic array of x-ray micro-beams is carried out by rotating the object.

17. The method of claim 1, wherein said contrast is greater than 20%.

18. The method of claim 1, wherein the common x-ray source comprises an array of x-ray generating microstructures.

19. An x-ray microscope system comprising:
a source of a periodic array of x-ray beams configured to impinge at least a portion of an object to be examined;
at least one x-ray pixel array detector comprising a plurality of pixels positioned to detect x-rays resulting from an interaction of said periodic array of x-ray beams with said object, the at least one x-ray pixel array detector producing at least one signal corresponding to said detected x-rays, and with said at least one x-ray pixel array detector aligned such that the x-rays detected by any single pixel of the plurality of pixels correspond to only one of the x-ray beams from among the periodic array of x-ray beams.

20. The x-ray microscope system of claim 19, wherein the source further comprises at least one x-ray filter configured to limit the bandwidth of the x-rays.

21. The x-ray microscope system of claim 20, wherein the at least one x-ray filter produces an x-ray spectrum having an average energy $E_0$ and an energy bandwidth within $E_0 \pm 15\%$.

22. The x-ray microscope system of claim 19, wherein the source comprises a grating structure to generate a Talbot interference pattern; and wherein the periodic array of x-ray beams corresponds to x-ray anti-nodes of the Talbot interference pattern and has a contrast between the Talbot anti-nodes and the neighboring Talbot nodes is greater than 10%.

23. The x-ray microscope system of claim 22, wherein the object to be examined and the pixels of the x-ray pixel array detector are both positioned within a depth-of-focus of the Talbot interference pattern.

24. The x-ray microscope system of claim 22, further comprising a mount configured to translate said object in two orthogonal directions.

25. The x-ray microscope system of claim 22, wherein the grating structure to generate a Talbot interference pattern comprises one or more of: an absorption grating, a $\pi/2$ phase shifting grating, an phase shifting grating, a 1-D array of grating structures, a 2-D array of grating structures, a grid structure, and a checkerboard phase grating structure.

26. The x-ray microscope system of claim 22, wherein the dimensions of the grating structure are selected such that the period of the period of the Talbot interference pattern is less than 50 micrometers.

27. The x-ray microscope system of claim 19, additionally comprising a mask positioned to block a predetermined number of the x-ray beams.

28. The x-ray microscope system of claim 19, wherein the x-ray pixel array detector is an energy resolving pixel array detector.

29. The x-ray microscope system of claim 19, additionally comprising a data collection and analysis system to analyze said at least one signal.

30. The x-ray microscope system of claim 19, wherein the source comprises:
a vacuum chamber;
an emitter for an electron beam; and
an electron target comprising: a substrate comprising a first material and, embedded in the substrate, at least a plurality of discrete structures comprising a second material configured to generate x-rays in response to electron bombardment.

31. The method of claim 1, wherein recording signals produced by said x-ray pixel array detector system comprises:
using a first detector of the x-ray pixel array detector system to detect x-rays from the object;
transmitting x-rays from the object through the first detector; and
using a second detector to detect x-rays transmitted through the first detector.

32. The x-ray microscope system of claim 19, wherein the at least one x-ray pixel array detector comprises:
a first x-ray pixel array detector comprising pixels and x-ray transmissive regions between the pixels; and
a second x-ray pixel array detector configured to detect x-rays transmitted through the x-ray transmissive regions of the first x-ray pixel array detector.

* * * * *

UNITED STATES PATENT AND TRADEMARK OFFICE
CERTIFICATE OF CORRECTION

PATENT NO. : 10,352,880 B2
APPLICATION NO. : 15/605957
DATED : July 16, 2019
INVENTOR(S) : Wenbing Yun Page 1 of 1

It is certified that error appears in the above-identified patent and that said Letters Patent is hereby corrected as shown below:

In the Specification

In Column 3, Line 15 (approx.), delete "t" and insert --π--.

In Column 9, Line 66, delete "t/2" and insert --π/2--.

In Column 13, Line 29, delete "micron)," and insert --micron$^2$),--.

In the Claims

In Column 16, Line 55, Claim 4, after "positioning" delete "placing".

Signed and Sealed this
Twelfth Day of November, 2019

Andrei Iancu
*Director of the United States Patent and Trademark Office*